United States Patent [19]

Marecki

[11] Patent Number: 6,006,745
[45] Date of Patent: Dec. 28, 1999

[54] DEVICE FOR DELIVERING AN AEROSOL

[75] Inventor: Paul E. Marecki, May Township, County of Washington, Minn.

[73] Assignee: Minnesota Mining and Manufacturing Company, St. Paul, Minn.

[21] Appl. No.: 08/443,355

[22] Filed: May 17, 1995

Related U.S. Application Data

[60] Continuation of application No. 08/184,645, Jan. 21, 1994, abandoned, which is a division of application No. 07/809,796, Dec. 18, 1991, Pat. No. 5,290,539, which is a continuation-in-part of application No. 07/632,133, Dec. 21, 1990, abandoned.

[51] Int. Cl.$^6$ .......................... A61M 11/04; B65D 83/14; B65D 83/54; C08F 210/08
[52] U.S. Cl. ............................. 128/200.23; 128/200.14; 128/200.21; 222/399; 222/402.1; 222/402.24; 222/402.25; 526/348.2; 526/348.4; 526/348.6; 424/45; 428/66.4
[58] Field of Search .............................. 526/348.2, 348.4, 526/348.6; 128/200.14, 200.21, 200.22, 200.23; 222/394, 354, 355, 402.1, 400.7, 402.24, 402.25; 424/43, 45

[56] References Cited

U.S. PATENT DOCUMENTS

| | | | |
|---|---|---|---|
| 2,721,010 | 10/1955 | Meshberg | 222/394 |
| 2,886,217 | 5/1959 | Thiel | 222/394 |
| 2,892,576 | 6/1959 | Ward | 222/394 |
| 2,968,427 | 1/1961 | Meshberg | 222/394 |
| 2,980,301 | 4/1961 | de Gorter | 222/394 |
| 3,049,269 | 8/1962 | Gawthrop | 222/307 |
| 3,052,382 | 9/1962 | Gawthrop | 222/335 |
| 3,702,310 | 11/1972 | Simons et al. | 252/430 |
| 3,727,806 | 4/1973 | Wilmot | 222/402.2 |
| 4,243,235 | 1/1981 | Repella | 277/152 |
| 4,298,721 | 11/1981 | Borghi et al. | 526/348 |
| 4,407,481 | 10/1983 | Bolton et al. | 251/353 |
| 4,429,079 | 1/1984 | Shibata et al. | 525/240 |
| 4,438,238 | 3/1984 | Fukushima et al. | 525/240 |
| 4,438,243 | 3/1984 | Kashiwa et al. | 526/125 |
| 4,526,385 | 7/1985 | Wheeler | 277/153 |
| 4,668,752 | 5/1987 | Tominari et al. | 526/348.2 |
| 4,819,834 | 4/1989 | Thiel | 222/355 |
| 4,822,855 | 4/1989 | Kobayashi et al. | 525/194 |
| 4,863,073 | 9/1989 | Burt et al. | 222/402.2 |
| 4,894,266 | 1/1990 | Bauer et al. | 428/35.4 |
| 5,001,205 | 3/1991 | Hoel | 526/128 |
| 5,002,048 | 3/1991 | Makiej, Jr. | 128/200.23 |
| 5,118,494 | 6/1992 | Schultz et al. | 424/45 |
| 5,126,123 | 6/1992 | Johnson | 424/45 |
| 5,158,775 | 10/1992 | Yazaki et al. | 424/45 |
| 5,182,097 | 1/1993 | Byron et al. | 424/45 |
| 5,190,029 | 3/1993 | Byron et al. | 128/200.14 |
| 5,192,548 | 3/1993 | Velasquez et al. | 424/443 |
| 5,290,539 | 3/1994 | Marecki | 424/45 |

FOREIGN PATENT DOCUMENTS

| | | |
|---|---|---|
| 2532714 | 3/1984 | France . |
| 63-20309 | 7/1986 | Japan . |
| 2033910 | 5/1980 | United Kingdom . |
| 2159091 | 11/1985 | United Kingdom . |
| 82/00470 | 2/1982 | WIPO . |

OTHER PUBLICATIONS

World Patents Index Latest, Derwent Publications Ltd., London, GB, AN 85–259656 & JP,A,60173047 (Dainippon) Sep. 6, 1985.
Union Carbide Flexomer™ Polyolefin Product Literature.

*Primary Examiner*—Paul J. Thibodeau
*Assistant Examiner*—Vivian Chen
*Attorney, Agent, or Firm*—Gary L. Griswold; Walter N. Kirn; Ted K. Ringsred

[57] ABSTRACT

A device for delivering an aerosol comprises a casing member, a valve stem, and a sealing member, wherein the sealing member comprises a thermoplastic elastomer comprising of a copolymer of about 80–95 mole % ethylene and about 5–20 mole % of at least one comonomer wherein the comonomer(s) are 1-butene, 1-hexene, or 1-octene. The device is used with pharmaceutical formulations containing 1,1,1,2-tetrafluoroethane and/or 1,1,1,2,3,3,3-heptafluoropropane as the propellant.

13 Claims, 1 Drawing Sheet

DEVICE FOR DELIVERING AN AEROSOL

This application is a continuation of U.S. application Ser. No. 08/184,645, filed Jan. 21, 1994 (now abandoned), which was a divisional of U.S. application Ser. No. 07/809,796, filed Dec. 18, 1991 (now U.S. Pat. No. 5,290,539), which was a continuation-in-part of U.S. application Ser. No. 07/632,133, filed Dec. 21, 1990 (now abandoned).

TECHNICAL FIELD

This invention relates to devices for delivering aerosols. In another aspect this invention relates to sealing members. In yet another aspect this invention relates to sealing members for use in devices for delivering aerosols. This invention also relates to thermoplastic polymer blends.

DESCRIPTION OF THE RELATED ART

The continuing use of aerosol formulations comprising conventional chlorofluorocarbon propellants is being debated due to the suspected role of such propellants in atmospheric depletion of ozone. Accordingly, alternative propellants such as HFC-134a (1,1,1,2-tetrafluoroethane) and HFC-227 (1,1,1,2,3,3,3-heptafluoropropane) are being developed to replace those conventional propellants thought to contribute to atmospheric ozone depletion.

Containers for aerosol formulations commonly include a rubber valve seal intended to allow reciprocal movement of the valve stem while preventing leakage of propellant from the container. These rubber valve seals are commonly made of thermoset rubbers such as butyl rubber, butadiene-acrylonitrile rubbers, ("Buna") and neoprene (polychloroisoprene), which are compounded with vulcanizing agents prior to being fashioned into valve seals.

SUMMARY OF THE INVENTION

It has been found that some conventional devices for delivering aerosols suffer impaired performance when used in connection with HFC-134a and/or HFC-227. Accordingly, this invention provides a device for delivering an aerosol, comprising: a valve stem, a diaphragm having walls defining a diaphragm aperture, and a casing member having walls defining a casing aperture, wherein the valve stem passes through the diaphragm aperture and the casing aperture and is in slidable sealing engagement with the diaphragm aperture, and wherein the diaphragm is in sealing engagement with the casing member, the diaphragm material comprising: a thermoplastic elastomer comprising a copolymer of about 80 to about 95 mole percent ethylene and a total of about 5 to about 20 mole percent of one or more comonomers selected from the group consisting of 1-butene, 1-hexene, or 1-octene (i.e., the total amount of comonomer in the copolymer is about 5 mole percent to about 20 mole percent).

This invention also provides a metered-dose device for delivering an aerosol that comprises, in addition to the above-discussed valve stem, diaphragm, and casing member, a tank seal having walls defining a tank seal aperture, and a metering tank of a predetermined volume and having an inlet end, an inlet aperture, and an outlet end, wherein the outlet end is in sealing engagement with the diaphragm, the valve stem passes through the inlet aperture and the tank seal aperture and is in slidable engagement with the tank seal aperture, and the tank seal is in sealing engagement with the inlet end of the metering tank, and wherein the valve stem is movable between an extended closed position, in which the inlet end of the metering tank is open and the outlet end is closed, and a compressed open position in which the inlet end of the metering tank is substantially sealed and the outlet end is open to the ambient atmosphere.

In a preferred embodiment the casing member defines a formulation chamber, and in a further preferred embodiment the formulation chamber contains an aerosol formulation comprising a propellant, said propellant comprising 1,1,1,2-tetrafluoroethane, 1,1,1,2,3,3,3-heptafluoropropane, or a mixture thereof.

In another aspect, this invention provides an elastomeric sealing member, e.g., for maintaining a desired atmosphere in a sealed chamber or for minimizing and/or preventing escape of propellants, such as 1,1,1,2-tetrafluoroethane or 1,1,1,2,3,3,3-heptafluoropropane, from a sealed chamber. Such sealing members can be used as appropriate in connection with static seals or dynamic seals, with pressurized or unpressurized systems, and with liquid or dry systems. The sealing member comprises a thermoplastic elastomer comprising a copolymer of about 80 to about 95 mole percent ethylene and a total of about 5 to about 20 mole percent of one or more comonomers selected from the group consisting of 1-butene, 1-hexene, and 1-octene. In a preferred embodiment the sealing member is used in a dynamic seal in a pressurized system in order to prevent escape of formulation components, such as 1,1,1,2-tetrafluoroethane or 1,1,1,2,3,3,3-heptafluoropropane, from a device for delivering an aerosol.

This invention also provides thermoplastic polymer blends comprising at least two thermoplastic copolymers, each comprising a copolymer of about 80 to about 95 mole percent ethylene and a total of about 5 to about 20 mole percent of one or more comonomers selected from the group consisting of 1-butene, 1-hexene, and 1-octene.

Devices, sealing members, and thermoplastic polymer blends of this invention find use in connection with aerosol formulations involving HFC-134a or HFC-227 as a propellant as well as with formulations containing other propellants such as chlorofluorocarbon propellants. Conventional devices involving thermoset diaphragms of neoprene (polychloroprene), butyl rubber, or butadiene-acrylonitrile "buna" copolymers allow excessive leakage of HFC-134a and HFC-227 from some formulations over time. Particularly in low volume formulations such as pharmaceutical formulations for use in inhalation therapy, this leakage can cause a substantial increase in concentration of the active ingredient in the formulation, resulting in delivery of an improper dose. Furthermore, with some formulations the valve stem tends to stick, pause, or drag during the actuation cycle when neoprene or butadiene-acrylonitrile "buna" diaphragms are used. Leakage and smoothness of operation are improved in the devices of the invention compared to like devices involving the conventional diaphragm materials. Hence this invention is particularly desirable for use with aerosol formulations wherein the propellant comprises HFC-134a, HFC-227, or a mixture thereof. Moreover, the thermoplastic elastomers used in the sealing members of the invention, including the thermoplastic polymer blends of the invention, are not compounded with vulcanizing agents and therefore they are free of complications that might arise from contamination by leaching of such vulcanizing agents.

BRIEF DESCRIPTION OF THE DRAWINGS

The drawing is represented by FIGS. 1 and 2.

DETAILED DESCRIPTION OF THE INVENTION

Figures 1, 2:
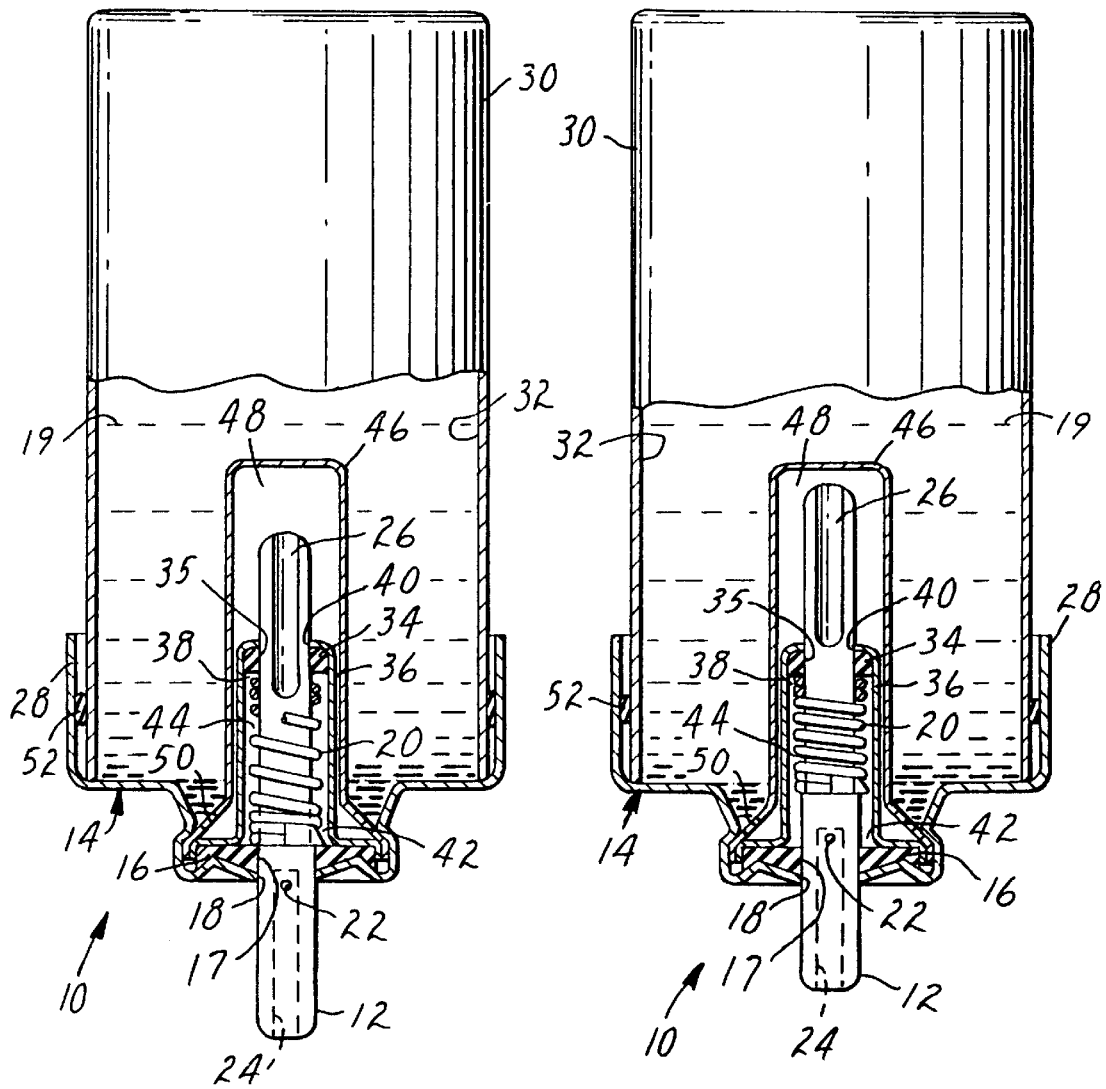
FIG. 1 is a partial cross-sectional view of one embodiment of a device of the invention, wherein the valve stem is in the extended closed position.
FIG. 2 is a partial cross-sectional view of the embodiment illustrated in FIG. 1, wherein the valve stem is in the compressed open position.

Unless otherwise indicated the copolymers described herein are random copolymers, i.e., the respective monomer units are substantially randomly distributed in the copolymer.

In order to minimize and/or prevent leakage of refrigerants, propellants, or other formulation components, especially propellants such as 1,1,1,2-tetrafluoroethane and 1,1,1,2,3,3,3-heptafluoropropane, from a sealed chamber, this invention provides thermoplastic elastomeric sealing members comprising a copolymer of about 80 to about 95 mole percent ethylene and a total of about 5 to about 20 mole percent of one or more comonomers selected from the group consisting of 1-butene, 1-hexene, and 1-octene. The thermoplastic elastomer can also contain minor amounts of conventional polymer additives such as processing aids, colorants, lubricants, and talc.

Suitable thermoplastic elastomers can be prepared using methods known to those skilled in the art. A preferred thermoplastic elastomer is FLEXOMER™ DFDA 1137 NT7 polyolefin (commercially available from Union Carbide), a thermoplastic elastomer comprising a copolymer of about 91 mole percent ethylene and about 9 mole percent 1-butene. This copolymer is said to have a density of 0.905 g/cm$^3$ (ASTM D-1505) and a melt index of 1.0 g/10 min (ASTM D-1238). FLEXOMER™ DFDA 1138 NT polyolefin (commercially available from Union Carbide), a thermoplastic elastomer comprising a copolymer of about 91 mole percent ethylene and about 9 mole percent 1-butene and having a density of 0.900 g/cm$^3$ (ASTM D-1505) and a melt index of 0.4 g/10 min (ASTM D-1238) is also suitable. A further suitable thermoplastic elastomer comprises a copolymer of about 88 mole percent ethylene and about 12 mole percent 1-butene. An example of such a thermoplastic elastomer is FLEXOMER™DEFD 8923 NT polyolefin (obtained on an experimental basis from Union Carbide). This elastomer is said to have a density of 0.890 g/cm$^3$ (ASTM D-1505), and a melt index of 1.0 g/10 min (ASTM D-1238).

Other exemplary suitable thermoplastic elastomers include:

FLEXOMER™ GERS 1085 NT polyolefin (Union Carbide), comprising a copolymer of about 80 mole percent ethylene and about 20 mole percent 1-butene, having a density of 0.884 g/cm$^3$ (ASTM D-1505) and a melt index of about 0.8 g/10 min (ASTM D 1238);

FLEXOMER™ DFDA 1163 NT7 polyolefin (Union Carbide), comprising a copolymer of about 95 mole percent ethylene, about 1 mole percent 1-butene, and about 4 mole percent 1-hexene, having a density of 0.910 g/cm$^3$ (ASTM D 1238) and a melt index of about 0.5 g/10 min (ASTM D 1238);

FLEXOMER™ DFDA 1164 NT7 polyolefin (Union Carbide), comprising a copolymer of about 94 mole percent ethylene, about 1 mole percent 1-butene, and about 5 mole percent 1-hexene, having a density of about 0.910 g/cm$^3$ (ASTM D 1505) and a melt index of about 1.0 g/10 min (ASTM D 1238).

FLEXOMER™ 1491 NT7 polyolefin (Union Carbide), comprising a copolymer of about 90 mole percent ethylene and about 10 mole percent 1-butene, having a density of 0.900 g/cm$^3$ (ASTM D 1505) and a melt index of about 1.0 g/10 min (ASTM D 1238);

FLEXOMER™ 9020 NT7 polyolefin (Union Carbide), comprising a copolymer of about 92 mole percent ethylene and about 8 mole percent 1-butene, having a density of 0.905 g/cm$^3$ (ASTM D 1505) and a melt index of about 0.85 g/10 min (ASTM D 1238);

FLEXOMER™ 9042 NT polyolefin (Union Carbide), comprising a copolymer of about 80 mole percent ethylene and about 20 mole percent 1-butene, having a density of 0.900 g/cm$^3$ (ASTM D 1505) and a melt index of about 5.0 g/10 min (ASTM D 1238).

ATTANE™ 4602 polyolefin (Dow), comprising a copolymer of about 90 mole percent ethylene and about 10 mole percent 1-octene, having a density of 0.912 g/cm$^3$ (ASTM D 792) and a melt index of about 3.3 g/10 min (ASTM D 1238);

ATTANE™ 4701 polyolefin (Dow), comprising a copolymer of about 92 mole percent ethylene and about 8 mole percent 1-octene, having a density of 0.912 g/cm$^3$ (ASTM D 792) and a melt index of about 1.0 g/10 min (ASTM D 1238).

Blends of two or more of the above-described thermoplastic elastomers in any proportion are also suitable. Preferred thermoplastic polymer blends of the invention include blends of two or more thermoplastic copolymers, each comprising about 80 to 95 mole percent ethylene and about 5 to about 20 mole percent 1-butene. More preferred are blends comprising (i) a copolymer of about 91 mole percent ethylene and about 9 mole percent 1-butene (e.g., FLEXOMER™ DFDA 1137 polyolefin), and (ii) a copolymer of about 80 mole percent ethylene and about 20 mole percent 1-butene (e.g., FLEXOMER™ GERS 1085 NT polyolefin). Blends comprising one part by weight of component (i) and about 0.25 to about 4 parts by weight of component (ii) are particularly preferred, especially for use in a dynamic seal and in a pressurized system, e.g., in a metered-dose inhaler.

The polymer blends of the invention can also comprise minor amounts of conventional polymer additives such as processing aids, colorants, lubricants, and talc.

As illustrated in the TABLES below, some of the seal materials and sealing members of the invention are superior to others for use in the dynamic seal of a pressurized aerosol container. Those seal materials that are less than optimal for use in the exemplified systems can nonetheless find use, e.g., in connection with a different general type of drug or a different valve stem than exemplified, as a static seal in a pressurized system, or in a non-pressurized system having a dynamic seal. The TABLES below occasionally contain data that appear somewhat inconsistent with other data (e.g., a single very high standard deviation as in TABLE 17). These aberrant results are generally attributable to failure of one or two vials in the test group.

The device of the invention will be described with reference to the Drawing. FIG. 1 shows device 10 comprising valve stem 12, casing member 14, and diaphragm 16. The casing member has walls defining casing aperture 18, and the diaphragm has walls defining diaphragm aperture 17. The valve stem passes through and is in slidable sealing engagement with the diaphragm aperture. The diaphragm is also in sealing engagement with casing member 14. Diaphragm 16 represents a thermoplastic elastomeric sealing member of the invention.

The illustrated embodiment is a device for use with pharmaceutical formulations. The diaphragm in the illustrated embodiment is of a thickness sufficient to form an effective seal with the casing member, preferably about 0.005 inch to about 0.050 inch. It has an outside diameter of about 0.340 inch, and an inside diameter sufficient to form an effective seal with the valve stem. As valve stems having an outside diameter of about 0.110 inch are commonly used, suitable diaphragm inside diameter can be in the range of about 0.080 inch to about 0.105 inch. Diaphragm dimensions suitable for use with other general types of devices can be easily selected by those skilled in the art.

Valve stem 12 is in slidable engagement with diaphragm aperture 17. Helical spring 20 holds the valve stem in an extended closed position as illustrated in FIG. 1. Valve stem 12 has walls defining orifice 22 which communicates with exit chamber 24 in the valve stem. The valve stem also has walls defining channel 26.

In the illustrated embodiment casing member 14 comprises mounting cup 28 and canister body 30 and defines formulation chamber 32. The illustrated embodiment further comprises tank seal 34 having walls defining tank seal aperture 35, and metering tank 36 having inlet end 38, inlet aperture 40, and outlet end 42. The metering tank also has walls defining metering chamber 44 of predetermined volume (e.g., 50 μL). Outlet end 42 of metering tank 36 is in sealing engagement with diaphragm 16, and valve stem 12 passes through inlet aperture 40 and is in slidable engagement with tank seal 34.

When device 10 is intended for use with a suspension aerosol formulation it further comprises retaining cup 46 fixed to mounting cup 28 and having walls defining retention chamber 48 and aperture 50. When intended for use with a solution aerosol formulation retaining cup 46 is optional. Also illustrated in device 10 is sealing member 52 in the form of an O-ring that substantially seals formulation chamber 32 defined by mounting cup 28 and canister body 30. Sealing member 52 preferably comprises the elastomeric copolymer described above.

Operation of device 10 is illustrated in FIGS. 1 and 2. In FIG. 1, the device is in the extended closed position. Aperture 50 allows open communication between retention chamber 48 and formulation chamber 32, thus allowing the aerosol formulation to enter the retention chamber. Channel 26 allows open communication between the retention chamber and metering chamber 44 thus allowing a predetermined amount of aerosol formulation to enter the metering chamber through inlet aperture 40. Diaphragm 16 seals outlet end 42 of the metering tank.

FIG. 2 shows device 10 in the compressed open position. As valve stem 12 is depressed channel 26 is moved relative to tank seal 34 such that inlet aperture 40 and tank seal aperture 35 are substantially sealed, thus isolating a metered dose of formulation within metering chamber 44. Further depression of the valve stem causes orifice 22 to pass through aperture 18 and into the metering chamber, whereupon the metered dose is exposed to ambient pressure. Rapid vaporization of the propellant causes the metered dose to be forced through the orifice, and into and through exit chamber 24. Device 10 is commonly used in combination with an actuator that facilitates inhalation of the resulting aerosol by a patient.

A particularly preferred device of the invention is a metered dose configuration substantially as described above and illustrated in the Drawing. Other particular configurations, metered dose or otherwise, are well known to those skilled in the art are suitable for use with the sealing members of this invention. For example the devices described in U.S. Pat. Nos. 4,819,834 (Thiel), 4,407,481 (Bolton), 3,052,382 (Gawthrop), 3,049,269 (Gawthrop), 2,980,301 (DeGorter), 2,968,427 (Meshberg), 2,892,576 (Ward), 2,886,217 (Thiel), and 2,721,010 (Meshberg) (all incorporated herein by reference) involve a valve stem, a diaphragm, and a casing member in the general relationship described herein. Generally any and all sealing members (such as diaphragms, seals, and gaskets) that serve to minimize and/or prevent escape of components, especially propellant, from such assemblies can comprise the above described thermoplastic elastomer.

The devices, sealing members, and polymer blends of the invention can be used in connection with aerosol formulations involving propellants such as fluorotrichloromethane, dichlorodifluoromethane, and 1,2-dichlorotetrafluoroethane. However, this invention finds particular use with aerosol formulations involving a propellant comprising HFC-134a or HFC-227. Any such formulation can be used. Pharmaceutical formulations are preferred.

Preferred pharmaceutical formulations generally comprise HFC-134a, HFC-227, or a mixture thereof in an amount effective to function as an aerosol propellant, a drug having local or systemic action and suitable for use by inhalation, and any optional formulation excipients. Exemplary drugs having local effect in the lung include bronchodilators such as albuterol, formoterol, pirbuterol, and salmeterol, and pharmaceutically acceptable salts and derivatives thereof, and steroids such as beclomethasone, fluticasone, and flunisolide, and pharmaceutically acceptable salts, derivatives, solvates, and clathrates thereof. Exemplary drugs having systemic effect include peptides such as insulin, calcitonin, interferons, colony stimulating factors, and growth factors.

The drug is present in the formulation in an amount sufficient to provide a predetermined number of therapeutically effective doses by inhalation, which can be easily determined by those skilled in the art considering the particular drug in the formulation. Optional excipients include cosolvents (e.g., ethanol, water) and surfactants (e.g., oleic acid, sorbitan esters, polyoxyethylenes, glycols) and others known to those skilled in the art.

A particularly preferred formulation comprises, by weight, 0.40% albuterol sulfate, 0.48% oleic acid, 14.26% absolute ethanol, and 84.86% HFC-134a. Another preferred formulation comprises, by weight, 0.337% beclomethasone dipropionate, 8.0% absolute ethanol, and 91.663% HFC-134a. Yet another preferred formulation comprises, by weight, 0.084% of beclomethasone dipropionate, 8.0% absolute ethanol, and 91.916% HFC-134a.

Blend Preparation

Polymer blends of the invention, from which sealing members of the invention can be made, can be prepared by conventional polymer blending techniques well known to those skilled in the art. Those blends exemplified herein were prepared as follows:

Small Scale Compounding

Selected quantities of the blend components are added to a heated 100 mL bowl in a BRABENDER™ laboratory mixer equipped with high shear mixing shafts. The components are mixed under temperature, speed, and time conditions selected according to the characteristics of the components of the blend. After mixing the mixing head is operated in reverse in order to expel the hot, mixed blend, which is compression molded as described below.

Large Scale Compounding

Selected quantities of the blend components are fed at room temperature into a APV Model 2030 TC twin screw extruder via feeders that are calibrated to match the extrusion rate.

Screw speed and extruder temperature are selected according to the characteristics of the components of the blend. The melt is extruded through a 0.63 cm (0.25 inch) strand dye having two strand openings. The strands are fed through a water bath, dried, and pelletized with a BERLYN™ Model Pe 112 chopper. The pellets are dried in trays for 1–3 days at about 50° C. and extruded into a sheet as described below.

Diaphragm Preparation Diaphragms of the invention can be prepared by conventional techniques known to those skilled in the art, such as compression molding, extrusion, and injection molding. Those diaphragms exemplified herein were prepared according to the general methods set forth below:

Compression Molding

An amount of a selected elastomer sufficient to provide a compression molded sheet of the desired thickness is compression molded between appropriately spaced aluminum press plates in a CARVER™ Laboratory Press Model 2696 (Fred S. Carver, Inc., Menomonie Falls, Wis.) at elevated temperature (e.g., about 150° C.) and pressure (e.g., 170 kPa) and for a time sufficient to form a molded sheet. The press is then cooled until the mold plates can be handled. The compression molded sheet is removed from the mold and hand punched with a die of the desired size to afford a diaphragm of the invention.

Extrusion

A sample of a selected elastomer is fed into the feed throat of a Haake RHEOCORT™ single-screw extruder fitted with a Haake RHEOMIX™ three-zone extruder head and equipped with a 1.9 cm (0.75 inch) diameter screw having a 3:1 pitch and a length to diameter ratio of 25:1. Appropriate screw speed and operating temperatures are selected according to the characteristics of the selected elastomer. The melt is extruded through a flat film die, fitted with a shim to provide the desire opening, and over a cooled chrome roller. The thickness of the resulting sheet is controlled by appropriate adjustment of screw speed and speed of the cooled roller. Diaphragms of the invention were hand cut from the sheet with a die of appropriate size.

Injection Molding

The selected elastomer is fed into the feed throat of a Van Dorn 75 ton injection molding machine equipped with a 5 ounce barrel. Operating conditions are selected according to the characteristics of the selected elastomer. The melt is injected into a mold having cavity dimensions appropriate to provide the desired sealing member. Cooling and opening of the mold affords the sealing member.

Test Methods

Sealing members were tested as follows:

Leak Rate

Aerosol canister bodies (10 mL) are filled with an aerosol formulation and fitted with a metered dose valve substantially as described and illustrated above and comprising a diaphragm of a selected size and material. The valve is actuated several times in order to assure its function. The mass of the filled device is measured. The filled device is allowed to stand in an upright position under the indicated conditions (30° C. unless otherwise indicated) for a period of time, after which time mass is again measured. The loss of mass over time is extrapolated to one year and reported in mg/year.

Valve Delivery

The mass of a filled device is measured. The device is then inverted and actuated one time. Mass is again determined and the valve delivery is recorded as the difference.

The formulations used in the TABLES below in order to demonstrate the invention are as follows, wherein all parts and percentages are by weight:

| Formulation | Albuterol Sulfate (%) | Beclomethasone Dipropionate (%) | Oleic Acid (%) | Ethanol (%) | HFC 134a (%) |
|---|---|---|---|---|---|
| A1 | 0.5 | — | 0.1 | 15 | 84.4 |
| A2 | 0.47 | — | 0.097 | 14.24 | 85.2 |
| A3 | 0.4 | — | 0.5 | 15 | 84.1 |
| A4 | 0.8 | — | 0.5 | 15 | 83.7 |
| A5 | 1.2 | — | 0.5 | 15 | 83.3 |
| A6 | 0.8 | — | 0.5 | 14.9 | 83.8 |
| B1 | — | 0.164 | — | 5.87 | 93.96 |
| B2 | — | 0.166 | — | 6.04 | 93.78 |
| B3 | — | 0.44 | — | 15 | 84.56 |
| D | — | — | 0.5 | 15.0 | 84.5 |
| P | Pirbuterol Acetate 0.89 | — | — | 10.0 | HFC-227 89.11 |
| A7 | Albuterol Sulfate 0.4 | — | — | | HFC-227 99.6 |

Diaphragms of FLEXOMER™ DEFD 8923 NT polyolefin were incorporated in a device substantially as described and illustrated above, and tested alongside devices comprising a neoprene diaphragm or a butadiene-acrylonitrile "buna" resin diaphragm. Results are shown in TABLE 1 below wherein "RH" designates relative humidity.

TABLE 1

LEAK RATE AND VALVE DELIVERY

| Diaphragm Material[1] | Formulation | Storage Condition | Time (Weeks) | N[2] | Leak Rate (mg/yr) | Valve Delivery (mg/actuation) |
|---|---|---|---|---|---|---|
| Buna | A5 | 30° C. | 0 | 25/15 | — | 46.46 ± 8.52 |
| | | " | 4 | " | 451 ± 71 | 48.90 ± 1.11 |
| | | " | 12 | " | 526 ± 76 | 49.64 ± 0.71 |
| Neoprene | A5 | 30° C. | 0 | 25/15 | — | 55.61 ± 0.69 |

TABLE 1-continued

LEAK RATE AND VALVE DELIVERY

| Diaphragm Material[1] | Formulation | Storage Condition | Time (Weeks) | N[2] | Leak Rate (mg/yr) | Valve Delivery (mg/actuation) |
|---|---|---|---|---|---|---|
| | | | 4 | " | 331 ± 54 | 55.31 ± 0.69 |
| | | | 12 | " | 395 ± 55 | 54.91 ± 0.92 |
| DEFD 8923 NT | A6 | 30° C. | 0 | 24/24 | — | 55.05 ± 1.64 |
| | | | 1 | " | 99 ± 17 | 55.09 ± 0.85 |
| | | | 2 | " | 135 ± 14 | 55.02 ± 1.50 |
| | | | 4 | " | 185 ± 11 | 54.28 ± 1.29 |
| DEFD 8923 NT | A6 | 40° C. 85% RH | 0 | 24/24 | — | 54.07 ± 3.48 |
| | | | 1 | " | 192 ± 17 | 54.20 ± 2.92 |
| | | | 2 | " | 288 ± 13 | 55.32 ± 1.03 |
| | | | 4 | " | 384 ± 12 | 54.54 ± 2.47 |
| DEFD 8923 NT | B3 | 30° C. | 0 | 24/24 | — | 57.39 ± 1.15 |
| | | | 1 | " | 108 ± 15 | 57.31 ± 0.79 |
| | | | 2 | " | 160 ± 13 | 57.08 ± 1.08 |
| | | | 4 | " | 223 ± 12 | 57.20 ± 0.89 |
| DEFD 8923 NT | B3 | 40° C. 85% RH | 0 | 24/24 | — | 57.43 ± 1.03 |
| | | | 1 | " | 286 ± 39 | 58.09 ± 2.52 |
| | | | 2 | " | 392 ± 34 | 58.78 ± 2.66 |
| | | | 4 | " | 491 ± 31 | 59.64 ± 3.40 |

[1] Buna and neoprene diaphragms from American Gasket and Rubber, Chicago1 Illinois. "DEFD 8923 NT" designates FLEXOMER ™ DEFD 8923NT polyolefin. All DEFD 8923 NT diaphragms were 0.035 inch thick with 0.095 inch inside diameter and 0.34 inch outside diameter. The buna and neoprene diaphragms were 0.038 inch thick with a 0.093 inch inside diameter and a 0.340 inch outside diameter. The valve stem had a 0.110 inch outside diameter.

[2] N is the number of vials per group. The first number of the pair is the number of valves whose individual measurements were averaged to give the reported leak rate. The second number of the pair is the number of individual measurements which were averaged to give the reported valve delivery.

The results in TABLE 1 show that, with the designated formulations using HFC-134a as the propellant, leak rates are substantially lower in the devices comprising the diaphragm of the invention than in the devices comprising diaphragms of materials that are commonly used in commercially available metered dose aerosol devices. Only under conditions of thermal stress (40° C., 85% RH) did the devices of the invention have leak rates comparable to those of the comparative devices tested at 30° C. Furthermore, valve delivery is more precise and more constant over time with devices of the invention than in the comparative devices of the prior art. Moreover, while the valves in the comparative devices often stuck, paused, or dragged during actuation, the valves in the devices of the invention generally exhibited smooth operation over the duration of the study.

Diaphragms of the invention of the specified composition and having a thickness of 0.035 inch, an outside diameter of 0.34 inch, and various inside diameters were tested with HFC-134a alone and with a model formulation (containing HFC-134a, ethanol, and a surfactant) in devices having either stainless steel ("ss") or DELRIN™ acetal resin (DuPont, "plastic") valve stems having a diameter of 0.110 inch. Results are shown in TABLE 2 (FLEXOMER™ DEFD 8923 NT polyolefin), TABLE 3 (FLEXOMER™ DFDA 1137 polyolefin), and TABLE 4 (FLEXOMER™ DFDA 1138 polyolefin) below, wherein each entry represents the mean of seven independent determinations.

TABLE 2

LEAK RATE AND VALVE DELIVERY WITH STAINLESS STEEL AND PLASTIC VALVE STEMS USING FLEXOMER ™ 8923 NT POLYOLEFIN DIAPHRAGMS HAVING VARIOUS INSIDE DIAMETERS

| Formulation | ID (in) | Stem | Time (Weeks) | Leak Rate (mg/yr) ± SD | Valve Delivery (mg/actuation) ± SD |
|---|---|---|---|---|---|
| 134a | 0.080 | ss | 0 | — | 86.90 ± 94.55 |
| | | | 5 | 34 ± 25 | 64.30 ± 1.30 |
| | | plastic | 0 | — | 61.86 ± 2.80 |
| | | | 5 | 26 ± 12 | 63.50 ± 0.62 |
| 134a | 0.085 | ss | 0 | — | 64.87 ± 7.61 |
| | | | 5 | 30 ± 17 | 61.34 ± 6.19 |
| | | plastic | 0 | — | 63.29 ± 0.60 |
| | | | 5 | 26 ± 13 | 63.27 ± 0.40 |
| 134a | 0.090 | ss | 0 | — | 64.44 ± 1.55 |
| | | | 5 | 26 ± 3 | 65.76 ± 2.30 |
| | | plastic | 0 | — | 63.63 ± 0.83 |
| | | | 5 | 40 ± 27 | 63.17 ± 0.72 |
| 134a | 0.095 | ss | 0 | — | 66.66 ± 1.11 |
| | | | 5 | 25 ± 2 | 68.03 ± 1.33 |
| | | plastic | 0 | — | 64.61 ± 0.98 |
| | | | 5 | 24 ± 3 | 64.63 ± 1.11 |
| 134a | 0.100 | ss | 0 | — | 58.79 ± 19.27 |
| | | | 5 | 27 ± 4 | 67.27 ± 0.99 |
| | | plastic | 0 | — | 65.07 ± 0.49 |
| | | | 5 | 33 ± 22 | 65.13 ± 0.73 |
| 134a | 0.105 | ss | 0 | — | 65.34 ± 1.80 |
| | | | 5 | 26 ± 2 | 66.84 ± 0.81 |
| | | plastic | 0 | — | 65.13 ± 0.79 |
| | | | 5 | 27 ± 4 | 65.14 ± 1.85 |
| D | 0.080 | ss | 0 | — | 61.26 ± 1.33 |
| | | | 5 | 147 ± 13 | 61.61 ± 1.26 |
| | | plastic | 0 | — | 60.46 ± 0.80 |
| | | | 5 | 143 ± 14 | 59.73 ± 0.73 |
| D | 0.085 | ss | 0 | — | 62.43 ± 1.00 |
| | | | 5 | 140 ± 19 | 62.71 ± 1.11 |
| | | plastic | 0 | — | 61.21 ± 0.75 |
| | | | 5 | 138 ± 6 | 60.46 ± 0.74 |

TABLE 2-continued

LEAK RATE AND VALVE DELIVERY WITH STAINLESS STEEL AND PLASTIC VALVE STEMS USING FLEXOMER ™ 8923 NT POLYOLEFIN DIAPHRAGMS HAVING VARIOUS INSIDE DIAMETERS

| Formulation | ID (in) | Stem | Time (Weeks) | Leak Rate (mg/yr) ± SD | Valve Delivery (mg/actuation) ± SD |
|---|---|---|---|---|---|
| D | 0.090 | ss | 0 | — | 61.81 ± 0.83 |
|   |   |   | 5 | 149 ± 20 | 62.07 ± 0.87 |
|   |   | plastic | 0 | — | 61.23 ± 0.56 |
|   |   |   | 5 | 140 ± 12 | 60.61 ± 0.41 |
| D | 0.095 | ss | 0 | — | 63.24 ± 0.73 |
|   |   |   | 5 | 154 ± 8 | 63.79 ± 0.81 |
|   |   | plastic | 0 | — | 62.26 ± 0.59 |
|   |   |   | 5 | 165 ± 12 | 62.07 ± 0.49 |
| D | 0.100 | ss | 0 | — | 62.99 ± 0.94 |
|   |   |   | 5 | 150 ± 10 | 63.61 ± 0.97 |
|   |   | plastic | 0 | — | 62.21 ± 1.03 |
|   |   |   | 5 | 167 ± 14 | 62.39 ± 0.67 |
| D | 0.105 | ss | 0 | — | 63.79 ± 0.66 |
|   |   |   | 5 | 163 ± 7 | 64.69 ± 0.64 |
|   |   | plastic | 0 | — | 61.66 ± 1.82 |
|   |   |   | 5 | 171 ± 9 | 61.77 ± 1.03 |

TABLE 3

LEAK RATE AND VALVE DELIVERY WITH STAINLESS STEEL AND PLASTIC VALVE STEMS USING FLEXOMER ™ 1137 POLYOLEFIN DIAPHRAGMS HAVING VARIOUS INSIDE DIAMETERS

| Formulation | ID (in) | Stem | Time (Weeks) | Leak Rate (mg/yr) ± SD | Valve Delivery (mg/actuation) ± SD |
|---|---|---|---|---|---|
| 134a | 0.080 | ss | 0 | — | 63.90 ± 9.37 |
|   |   |   | 5 | 28.4 ± 3.4 | 67.14 ± 0.83 |
|   |   | plastic | 0 | — | 62.73 ± 3.40 |
|   |   |   | 5 | 28.6 ± 6.7 | 61.91 ± 3.21 |
| 134a | 0.085 | ss | 0 | — | 67.57 ± 17.25 |
|   |   |   | 5 | 30.7 ± 6.8 | 67.77 ± 3.59 |
|   |   | plastic | 0 | — | 61.41 ± 4.20 |
|   |   |   | 5 | 29.6 ± 11.0 | 60.90 ± 7.20 |
| 134a | 0.090 | ss | 0 | — | 58.90 ± 19.00 |
|   |   |   | 5 | 34.6 ± 6.7 | 66.80 ± 0.88 |
|   |   | plastic | 0 | — | 62.07 ± 3.78 |
|   |   |   | 5 | 27.7 ± 4.2 | 61.23 ± 6.49 |
| 134a | 0.095 | ss | 0 | — | 59.83 ± 15.34 |
|   |   |   | 5 | 25.9 ± 5.9 | 66.67 ± 0.67 |
|   |   | plastic | 0 | — | 65.01 ± 0.95 |
|   |   |   | 5 | 32.8 ± 18.5 | 65.16 ± 0.72 |
| 134a | 0.100 | ss | 0 | — | 66.69 ± 0.57 |
|   |   |   | 5 | 30.6 ± 3.6 | 67.14 ± 0.76 |
|   |   | plastic | 0 | — | 64.36 ± 2.31 |
|   |   |   | 5 | 30.7 ± 6.9 | 65.74 ± 1.01 |
| 143a | 0.105 | ss | 0 | — | 56.66 ± 14.38 |
|   |   |   | 5 | 39.0 ± 11.4 | 67.81 ± 3.58 |
|   |   | plastic | 0 | — | 62.77 ± 3.25 |
|   |   |   | 5 | 39.8 ± 16.6 | 65.41 ± 1.83 |
| D | 0.080 | ss | 0 | — | 59.34 ± 4.75 |
|   |   |   | 5 | 163 ± 30.8 | 62.84 ± 0.53 |
|   |   | plastic | 0 | — | 56.31 ± 5.38 |
|   |   |   | 5 | 197 ± 34.1 | 61.04 ± 0.26 |
| D | 0.085 | ss | 0 | — | 61.83 ± 1.64 |
|   |   |   | 5 | 179 ± 61.8 | 63.13 ± 0.87 |
|   |   | plastic | 0 | — | 59.59 ± 2.41 |
|   |   |   | 5 | 156 ± 16.4 | 60.74 ± 0.37 |
| D | 0.090 | ss | 0 | — | 60.83 ± 2.39 |
|   |   |   | 5 | 169 ± 40.8 | 61.90 ± 2.31 |
|   |   | plastic | 0 | — | 59.04 ± 1.31 |
|   |   |   | 5 | 225 ± 31.0 | 60.10 ± 2.66 |
| D | 0.095 | ss | 0 | — | 59.59 ± 4.07 |
|   |   |   | 5 | 210 ± 53.0 | 60.00 ± 3.66 |
|   |   | plastic | 0 | — | 54.99 ± 5.41 |
|   |   |   | 5 | 243 ± 35.9 | 56.20 ± 1.58 |
| D | 0.100 | ss | 0 | — | 61.49 ± 1.37 |
|   |   |   | 5 | 187 ± 12.9 | 61.41 ± 1.25 |
|   |   | plastic | 0 | — | 54.89 ± 3.36 |
|   |   |   | 5 | 282 ± 11.8 | 56.14 ± 1.95 |
| D | 0.105 | ss | 0 | — | 50.81 ± 5.07 |
|   |   |   | 5 | 200 ± 11.9 | 53.00 ± 3.28 |
|   |   | plastic | 0 | — | 48.43 ± 2.57 |
|   |   |   | 5 | 232 ± 30.8 | 48.51 ± 1.02 |

TABLE 4

LEAK RATE AND VALVE DELIVERY WITH STAINLESS STEEL AND PLASTIC VALVE STEMS USING FLEXOMER ™ 1138 POLYOLEFIN DIAPHRAGMS HAVING VARIOUS INSIDE DIAMETERS

| Formulation | ID (in) | Stem | Time (Weeks) | Leak Rate (mg/yr) ± SD | Valve Delivery (mg/actuation) ± SD |
|---|---|---|---|---|---|
| 134a | 0.080 | ss | 0 | — | 66.17 ± 56.10 |
|   |   |   | 5 | 16.4 ± 2.51 | 63.03 ± 20.22 |
|   |   | plastic | 0 | — | 62.27 ± 6.85 |
|   |   |   | 5 | 14.9 ± 1.8 | 64.89 ± 1.30 |
| 134a | 0.085 | ss | 0 | — | 59.77 ± 18.00 |
|   |   |   | 5 | 36.8 ± 44.4 | 64.77 ± 17.07 |
|   |   | plastic | 0 | — | 69.40 ± 15.00 |
|   |   |   | 5 | 15.0 ± 3.9 | 65.26 ± 1.07 |
| 134a | 0.090 | ss | 0 | — | 52.64 ± 18.28 |
|   |   |   | 5 | 45.7 ± 43.5 | 68.67 ± 2.12 |
|   |   | plastic | 0 | — | 57.86 ± 15.78 |
|   |   |   | 5 | 14.8 ± 3.6 | 70.34 ± 8.47 |
| 134a | 0.095 | ss | 0 | — | 57.57 ± 17.59 |
|   |   |   | 5 | 22.5 ± 7.3 | 68.43 ± 1.07 |
|   |   | plastic | 0 | — | 64.84 ± 1.69 |
|   |   |   | 5 | 14.5 ± 3.4 | 65.97 ± 2.67 |
| 134a | 0.100 | ss | 0 | — | 59.70 ± 20.32 |
|   |   |   | 5 | 20.3 ± 7.3 | 67.59 ± 1.95 |
|   |   | plastic | 0 | — | 64.79 ± 0.61 |
|   |   |   | 5 | 21.1 ± 18.8 | 65.53 ± 0.72 |
| 134a | 0.105 | ss | 0 | — | 65.64 ± 0.90 |
|   |   |   | 5 | 23.7 ± 3.0 | 67.34 ± 0.80 |
|   |   | plastic | 0 | — | 65.11 ± 1.67 |
|   |   |   | 5 | 17.4 ± 3.4 | 68.56 ± 3.86 |
| D | 0.080 | ss | 0 | — | 60.23 ± 0.57 |
|   |   |   | 5 | 187 ± 14.3 | 60.90 ± 0.63 |
|   |   | plastic | 0 | — | 58.41 ± 0.52 |
|   |   |   | 5 | 204 ± 6.2 | 50.16 ± 22.12 |
| D | 0.085 | ss | 0 | — | 60.74 ± 1.12 |
|   |   |   | 5 | 178 ± 5.4 | 61.30 ± 0.92 |
|   |   | plastic | 0 | — | 58.43 ± 0.45 |
|   |   |   | 5 | 220 ± 30.4 | 59.04 ± 2.10 |
| D | 0.090 | ss | 0 | — | 60.11 ± 1.36 |
|   |   |   | 5 | 237 ± 42.8 | 61.04 ± 1.39 |
|   |   | plastic | 0 | — | 56.87 ± 0.79 |
|   |   |   | 5 | 258 ± 24.5 | 56.36 ± 1.01 |
| D | 0.095 | ss | 0 | — | 58.37 ± 5.54 |
|   |   |   | 5 | 252 ± 40.8 | 60.69 ± 1.98 |
|   |   | plastic | 0 | — | 52.76 ± 6.49 |
|   |   |   | 5 | 270 ± 21.6 | 55.26 ± 1.52 |
| D | 0.100 | ss | 0 | — | 58.66 ± 0.45 |
|   |   |   | 5 | 217 ± 13.3 | 58.60 ± 0.60 |
|   |   | plastic | 0 | — | 56.97 ± 1.37 |
|   |   |   | 5 | 288 ± 74.6 | 56.66 ± 1.87 |
| D | 0.105 | ss | 0 | — | 58.31 ± 0.85 |
|   |   |   | 5 | 243 ± 16.3 | 58.51 ± 0.85 |
|   |   | plastic | 0 | — | 57.40 ± 0.98 |
|   |   |   | 5 | 251 ± 11.0 | 56.61 ± 0.52 |

The results in TABLES 2, 3, and 4 show that diaphragms of the invention having various inside diameters afford low leak rates and reproducible valve delivery with stainless steel ("ss") and DELRIN™ acetal resin ("plastic") valve stems when used with the designated formulations. Leak rate results with the ethanol-containing formulation, while not as low as with only HFC-134a, compare favorably to the data in TABLE 1 involving buna and neoprene diaphragms. Furthermore, the valves in the devices of the invention generally exhibited smooth operation over the duration of the study.

Diaphragms of the invention prepared from FLEXOMER™DEFD 8923 NT polyolefin and having an inside diameter of 0.090 inch and various specified thicknesses were tested with HFC-134a alone or with a model formulation (containing HFC-134a, ethanol, and a surfactant) in devices comprising either stainless steel ("ss") or DELRIN™ acetal resin ("plastic") valve stems. Results are shown in TABLE 5 below, wherein each entry represents the mean of 7 independent determinations.

TABLE 5

LEAK RATE USING FLEXOMER ™ 8923 NT
POLYOLEFIN DIAPHRAGMS OF VARIOUS THICKNESSES

| Formulation | Thickness (in) | Stem | Time (Weeks) | Leak Rate (mg/yr) ± SD |
|---|---|---|---|---|
| 134a | 0.038 | ss | 0 | — |
|  |  |  | 5 | 25.8 ± 4.0 |
|  |  | plastic | 0 | — |
|  |  |  | 5 | 24.6 ± 3.9 |
| 134a | 0.035 | ss | 0 | — |
|  |  |  | 5 | 27.3 ± 4.3 |
|  |  | plastic | 0 | — |
|  |  |  | 5 | 48.5 ± 66.0 |
| 134a | 0.029 | ss | 0 | — |
|  |  |  | 5 | 24.5 ± 2.0 |
|  |  | plastic | 0 | — |
|  |  |  | 5 | 22.2 ± 3.5 |
| 134a | 0.025 | ss | 0 | — |
|  |  |  | 5 | 24.5 ± 6.5 |
|  |  | plastic | 0 | — |
|  |  |  | 5 | 24.5 ± 11 |
| 134a | 0.020 | ss | 0 | — |
|  |  |  | 5 | 21.9 ± 2.5 |
|  |  | plastic | 0 | — |
|  |  |  | 5 | 20.0 ± 1.6 |
| 134a | 0.015 | ss | 0 | — |
|  |  |  | 5 | 22.2 ± 2.6 |
|  |  | plastic | 0 | — |
|  |  |  | 5 | 50.0 ± 2.6 |
| 134a | 0.010 | ss | 0 | — |
|  |  |  | 5 | 46.7 ± 38.7 |
|  |  | plastic | 0 | — |
|  |  |  | 5 | 16.5 ± 2.3 |
| D | 0.038 | ss | 0 | — |
|  |  |  | 5 | 200 ± 17 |
|  |  | plastic | 0 | — |
|  |  |  | 5 | 217 ± 14 |
| D | 0.035 | ss | 0 | — |
|  |  |  | 5 | 185 ± 8.7 |
|  |  | plastic | 0 | — |
|  |  |  | 5 | 209 ± 12 |
| D | 0.029 | ss | 0 | — |
|  |  |  | 5 | 182 ± 2.5 |
|  |  | plastic | 0 | — |
|  |  |  | 5 | 201 ± 12 |
| D | 0.025 | ss | 0 | — |
|  |  |  | 5 | 176 ± 6.4 |
|  |  | plastic | 0 | — |
|  |  |  | 5 | 210 ± 4.8 |
| D | 0.020 | ss | 0 | — |
|  |  |  | 5 | 190 ± 6.5 |
|  |  | plastic | 0 | — |
|  |  |  | 5 | 207 ± 7.4 |
| D | 0.015 | ss | 0 | — |
|  |  |  | 5 | 182 ± 7.8 |

TABLE 5-continued

LEAK RATE USING FLEXOMER ™ 8923 NT
POLYOLEFIN DIAPHRAGMS OF VARIOUS THICKNESSES

| Formulation | Thickness (in) | Stem | Time (Weeks) | Leak Rate (mg/yr) ± SD |
|---|---|---|---|---|
|  |  | plastic | 0 | — |
|  |  |  | 5 | 196 ± 6.4 |
| D | 0.010 | ss | 0 | — |
|  |  |  | 5 | 180 ± 5.4 |
|  |  | plastic | 0 | — |
|  |  |  | 5 | 201 ± 20 |

The results in TABLE 5 show that with the designated formulations leak rate is lower in devices comprising a diaphragm of the invention than in devices such as those tested in connection with TABLE 1 above comprising a buna or neoprene diaphragm. TABLE 5 also shows that relatively thin diaphragms can be used with little or no loss of performance.

In the TABLES that follow, the inside diameter of the diaphragms (ID) is given in thousandths of an inch, "pl" represents a valve stem made of DELRIN™ acetal resin (DuPont) having a diameter of 0.110 inch, and "N" refers to the number of independent determinations used in calculating the leak rate and valve delivery values.

Diaphragms of the invention were prepared by compression molding, injection molding, and extrusion from FLEXOMER™ GERS 1085 NT polyolefin and tested with the formulations indicated in TABLES 6–8 below.

TABLE 6

COMPRESSION MOLDED FLEXOMER ™
GERS 1085 NT POLYOLEFIN

| Formulation | ID | Stem | Time (Weeks) | N | Leak Rate (mg/yr) | Valve Delivery (mg/actuation) |
|---|---|---|---|---|---|---|
| A1 | 80 | ss | 0 | 14 | — | 56.81 ± 0.74 |
|  |  |  | 6 |  | 243 ± 10 | 57.18 ± 0.82 |
|  | 85 | ss | 0 | 14 | — | 55.94 ± 3.64 |
|  |  |  | 6 |  | 247 ± 10 | 58.74 ± 1.26 |
|  | 90 | ss | 0 | 14 | — | 58.09 ± 6.45 |
|  |  |  | 6 |  | 240 ± 9 | 59.74 ± 2.92 |
|  | 95 | ss | 0 | 14 | — | 58.40 ± 0.95 |
|  |  |  | 6 |  | 231 ± 12 | 59.33 ± 1.44 |
|  | 100 | ss | 0 | 14 | — | 58.41 ± 1.46 |
|  |  |  | 6 |  | 227 ± 8 | 60.40 ± 2.78 |
|  | 105 | ss | 0 | 14 | — | 55.94 ± 7.25 |
|  |  |  | 6 |  | 224 ± 8 | 62.52 ± 3.77 |
|  | 80 | pl | 0 | 14 | — | 55.91 ± 1.48 |
|  |  |  | 6 |  | 270 ± 6 | 55.62 ± 0.68 |
|  | 85 | pl | 0 | 14 | — | 54.22 ± 4.63 |
|  |  |  | 6 |  | 270 ± 11 | 56.71 ± 2.22 |
|  | 90 | pl | 0 | 14 | — | 57.42 ± 4.56 |
|  |  |  | 6 |  | 265 ± 16 | 58.67 ± 2.13 |
|  | 95 | pl | 0 | 14 | — | 56.10 ± 4.14 |
|  |  |  | 6 |  | 260 ± 8 | 58.67 ± 1.72 |
|  | 100 | pl | 0 | 14 | — | 58.73 ± 3.30 |
|  |  |  | 6 |  | 256 ± 14 | 60.96 ± 3.72 |
|  | 105 | pl | 0 | 14 | — | 57.96 ± 3.17 |
|  |  |  | 6 |  | 243 ± 11 | 61.50 ± 1.35 |

TABLE 7

INJECTION MOLDED FLEXOMER ™ GERS 1085 NT POLYOLEFIN

| Formulation | ID | Stem | Time (Weeks) | N | Leak Rate (mg/yr) | Valve Delivery (mg/actuation) |
|---|---|---|---|---|---|---|
| A1 | 84 | ss | 0 | 10 | — | 57.70 ± 1.06 |
|  |  |  | 6 |  | 263 ± 8 | 59.17 ± 1.12 |
|  | 88 | ss | 0 | 10 | — | 56.51 ± 2.98 |
|  |  |  | 6 |  | 275 ± 10 | 60.21 ± 2.34 |
|  | 94 | ss | 0 | 10 | — | 58.87 ± 1.85 |
|  |  |  | 6 |  | 286 ± 12 | 58.70 ± 0.64 |
|  | 99 | ss | 0 | 10 | — | 58.12 ± 0.54 |
|  |  |  | 6 |  | 269 ± 11 | 59.48 ± 2.75 |
|  | 84 | pl | 0 | 10 | — | 55.49 ± 2.52 |
|  |  |  | 6 |  | 267 ± 9 | 55.92 ± 1.81 |
|  | 88 | pl | 0 | 10 | — | 56.33 ± 0.34 |
|  |  |  | 6 |  | 284 ± 11 | 56.56 ± 0.24 |
|  | 94 | pl | 0 | 10 | — | 56.21 ± 1.23 |
|  |  |  | 6 |  | 286 ± 10 | 56.72 ± 0.42 |
|  | 99 | pl | 0 | 10 | — | 55.35 ± 2.74 |
|  |  |  | 6 |  | 282 ± 11 | 56.54 ± 0.99 |
| B1 | 84 | ss | 0 | 10 | — | 62.18 ± 0.92 |
|  |  |  | 6 |  | 231 ± 16 | 63.24 ± 1.26 |
|  | 88 | ss | 0 | 10 | — | 61.93 ± 0.50 |
|  |  |  | 6 |  | 232 ± 11 | 64.20 ± 3.20 |
|  | 94 | ss | 0 | 10 | — | 62.45 ± 0.79 |
|  |  |  | 6 |  | 243 ± 11 | 63.78 ± 1.47 |
|  | 99 | ss | 0 | 10 | — | 63.40 ± 2.61 |
|  |  |  | 6 |  | 240 ± 10 | 63.56 ± 1.92 |
| B1 | 84 | pl | 0 | 10 | — | 60.47 ± 0.42 |
|  |  |  | 6 |  | 256 ± 13 | 60.37 ± 0.53 |
|  | 88 | pl | 0 | 10 | — | 60.29 ± 0.78 |
|  |  |  | 6 |  | 246 ± 10 | 60.57 ± 0.45 |
|  | 94 | pl | 0 | 10 | — | 60.75 ± 0.96 |
|  |  |  | 6 |  | 251 ± 10 | 60.73 ± 0.64 |
|  | 99 | pl | 0 | 10 | — | 59.43 ± 3.11 |
|  |  |  | 6 |  | 264 ± 22 | 60.46 ± 0.45 |

TABLE 8

EXTRUDED FLEXOMER ™ GERS 1085 NT POLYOLEFIN

| Formulation | ID | Stem | Time (Weeks) | N | Leak Rate (mg/yr) | Valve Delivery (mg/actuation) |
|---|---|---|---|---|---|---|
| A2 | 80 | ss | 0 | 10 | — | 58.26 ± 2.17 |
|  |  |  | 6 |  | 279 ± 9 | 57.76 ± 0.96 |
|  | 85 | ss | 0 | 10 | — | 57.49 ± 2.24 |
|  |  |  | 6 |  | 274 ± 15 | 57.99 ± 2.23 |
|  | 90 | ss | 0 | 10 | — | 58.66 ± 1.91 |
|  |  |  | 6 |  | 274 ± 15 | 58.01 ± 0.66 |
|  | 95 | ss | 0 | 10 | — | 57.29 ± 2.97 |
|  |  |  | 6 |  | 282 ± 18 | 58.30 ± 1.11 |
|  | 100 | ss | 0 | 10 | — | 58.49 ± 1.64 |
|  |  |  | 6 |  | 284 ± 18 | 58.16 ± 0.77 |
|  | 105 | ss | 0 | 10 | — | 57.97 ± 1.40 |
|  |  |  | 6 |  | 307 ± 11 | 57.99 ± 1.10 |
|  | 80 | pl | 0 | 10 | — | 55.91 ± 0.69 |
|  |  |  | 6 |  | 270 ± 14 | 55.50 ± 0.66 |
|  | 85 | pl | 0 | 10 | — | 55.18 ± 1.41 |
|  |  |  | 6 |  | 275 ± 8 | 55.25 ± 0.48 |
|  | 90 | pl | 0 | 10 | — | 56.38 ± 0.66 |
|  |  |  | 6 |  | 277 ± 12 | 55.54 ± 0.53 |
|  | 95 | pl | 0 | 10 | — | 56.68 ± 0.71 |
|  |  |  | 6 |  | 264 ± 14 | 55.67 ± 0.58 |
|  | 100 | pl | 0 | 10 | — | 56.37 ± 0.70 |
|  |  |  | 6 |  | 282 ± 13 | 55.41 ± 0.51 |
|  | 105 | pl | 0 | 10 | — | 56.38 ± 0.65 |
|  |  |  | 6 |  | 318 ± 25 | 55.56 ± 0.64 |
| A3 | 80 | ss | 0 | 10 | — | 58.35 ± 0.74 |
|  |  |  | 6 |  | 232 ± 18 | not measured |
|  | 85 | ss | 0 | 10 | — | 58.35 ± 1.00 |
|  |  |  | 6 |  | 233 ± 20 | 57.96 ± 0.92 |
|  | 90 | ss | 0 | 10 | — | 57.60 ± 2.61 |
|  |  |  | 6 |  | 247 ± 62 | 57.85 ± 0.87 |
|  | 95 | ss | 0 | 10 | — | 58.82 ± 0.73 |
|  |  |  | 6 |  | 226 ± 22 | 58.41 ± 0.74 |
|  | 100 | ss | 0 | 10 | — | 58.97 ± 0.83 |
|  |  |  | 6 |  | 231 ± 23 | 58.59 ± 0.65 |
|  | 105 | ss | 0 | 10 | — | 58.87 ± 1.02 |
|  |  |  | 6 |  | 253 ± 22 | not measured |
|  | 80 | pl | 0 | 10 | — | 55.98 ± 0.55 |
|  |  |  | 6 |  | 236 ± 13 | 54.97 ± 0.35 |
|  | 85 | pl | 0 | 10 | — | 56.17 ± 0.50 |
|  |  |  | 6 |  | 239 ± 15 | 54.65 ± 0.72 |
|  | 90 | pl | 0 | 10 | — | 56.27 ± 0.55 |
|  |  |  | 6 |  | 230 ± 9 | 55.01 ± 0.58 |
|  | 95 | pl | 0 | 10 | — | 56.78 ± 1.80 |
|  |  |  | 6 |  | 239 ± 20 | 55.93 ± 0.52 |
|  | 100 | pl | 0 | 10 | — | 57.38 ± 0.69 |
|  |  |  | 6 |  | 231 ± 11 | 55.95 ± 0.74 |
|  | 105 | pl | 0 | 10 | — | 57.34 ± 0.70 |
|  |  |  | 6 |  | 245 ± 16 | 55.56 ± 0.49 |
| B2 | 80 | ss | 0 | 10 | — | 60.32 ± 3.80 |
|  |  |  | 6 |  | 157 ± 16 | 62.60 ± 0.94 |
| B2 | 85 | ss | 0 | 10 | — | 62.49 ± 1.02 |
|  |  |  | 6 |  | 190 ± 60 | 63.34 ± 0.78 |
|  | 90 | ss | 0 | 10 | — | 62.68 ± 0.89 |
|  |  |  | 6 |  | 153 ± 11 | 63.16 ± 0.71 |
|  | 95 | ss | 0 | 10 | — | 62.60 ± 0.66 |
|  |  |  | 6 |  | 156 ± 10 | 64.36 ± 3.29 |
|  | 100 | ss | 0 | 10 | — | 63.39 ± 2.36 |
|  |  |  | 6 |  | 155 ± 10 | 65.12 ± 2.70 |
|  | 105 | ss | 0 | 10 | — | 64.08 ± 1.67 |
|  |  |  | 6 |  | 155 ± 7 | 64.39 ± 0.85 |
|  | 80 | pl | 0 | 10 | — | 61.20 ± 3.22 |
|  |  |  | 6 |  | 158 ± 9 | 59.90 ± 0.33 |
|  | 85 | pl | 0 | 10 | — | 60.15 ± 1.02 |
|  |  |  | 6 |  | 156 ± 11 | 60.05 ± 0.71 |
|  | 90 | pl | 0 | 10 | — | 60.95 ± 2.00 |
|  |  |  | 6 |  | 158 ± 28 | 60.14 ± 0.68 |
|  | 95 | pl | 0 | 10 | — | 54.61 ± 19.10 |
|  |  |  | 6 |  | 158 ± 7 | 60.94 ± 0.59 |
|  | 100 | pl | 0 | 10 | — | 61.05 ± 1.37 |
|  |  |  | 6 |  | 153 ± 10 | 61.71 ± 2.26 |
|  | 105 | pl | 0 | 10 | — | 60.85 ± 0.62 |
|  |  |  | 6 |  | 154 ± 9 | 60.71 ± 0.66 |

The results in TABLES 6–8 show that these diaphragms of the invention exhibit acceptable leak rate and valve delivery variability when used with the indicated formulations, regardless of the method of preparation or the valve stem material.

Diaphragms of the invention were prepared by injection molding and by compression molding from FLEXOMER™ DFDA 1137 NT 7 polyolefin and tested with the formulations indicated in TABLES 9A and 9B below.

TABLE 9 A

INJECTION MOLDED FLEXOMER ™ DFDA 1137 POLYOLEFIN

| Formulation | ID | Stem | Time (Weeks) | N | Leak Rate (mg/yr) | Valve Delivery (mg/actuation) |
|---|---|---|---|---|---|---|
| A2 | 84 | ss | 0 | 10 | — | 61.51 ± 2.04 |
|  |  |  | 6 |  | 297 ± 41 | 61.79 ± 1.78 |
|  | 88 | ss | 0 | 10 | — | 59.56 ± 0.80 |
|  |  |  | 6 |  | 298 ± 35 | 61.28 ± 3.39 |
|  | 94 | ss | 0 | 10 | — | 61.57 ± 3.81 |
|  |  |  | 6 |  | 312 ± 18 | 66.49 ± 7.58 |
|  | 98 | ss | 0 | 10 | — | 61.88 ± 5.25 |
|  |  |  | 6 |  | 289 ± 17 | 63.31 ± 7.20 |
|  | 84 | pl | 0 | 10 | — | 60.88 ± 2.38 |
|  |  |  | 6 |  | 298 ± 32 | 59.47 ± 1.12 |

TABLE 9 A-continued

INJECTION MOLDED FLEXOMER™ DFDA 1137 POLYOLEFIN

| Formulation | ID | Stem | Time (Weeks) | N | Leak Rate (mg/yr) | Valve Delivery (mg/actuation) |
|---|---|---|---|---|---|---|
|  | 88 | pl | 0 | 10 | — | 59.68 ± 1.80 |
|  |  |  | 6 |  | 288 ± 35 | 59.33 ± 1.25 |
|  | 94 | pl | 0 | 10 | — | 59.14 ± 1.05 |
|  |  |  | 6 |  | 303 ± 23 | 61.38 ± 4.29 |
|  | 98 | pl | 0 | 10 | — | 58.81 ± 2.06 |
|  |  |  | 6 |  | 292 ± 16 | 60.56 ± 1.75 |

TABLE 9 B

COMPRESSION MOLDED FLEXOMER™ DFDA 1137 NT 7 POLYOLEFIN

| Formulation | ID | Stem | Time (Weeks) | N | Leak Rate (mg/yr) | Valve Delivery (mg/actuation) |
|---|---|---|---|---|---|---|
| A4 | 84 | pl | 0 | 24 | — | 53.14 ± 7.34 |
|  |  |  | 2 |  | 198 ± 51 | 56.13 ± 0.99 |
|  |  |  | 4 |  | 249 ± 50 | 54.71 ± 3.07 |
|  |  |  | 8 |  | 296 ± 50 | 55.60 ± 1.55 |
|  |  |  | 12 |  | 330 ± 52 | 53.96 ± 7.10 |
|  |  |  | 24 |  | 361 ± 52 | 54.62 ± 5.58 |
| B3 | 95 | pl | 0 | 24 | — | 56.09 ± 2.41 |
|  |  |  | 2 |  | 221 ± 26 | 57.07 ± 1.27 |
|  |  |  | 4 |  | 265 ± 27 | 56.67 ± 1.67 |
|  |  |  | 8 |  | 311 ± 29 | 57.25 ± 1.61 |
|  |  |  | 12 |  | 345 ± 31 | 57.32 ± 2.23 |
|  |  |  | 24 |  | 373 ± 32 | 59.10 ± 3.22 |

The results in TABLES 9A and 9B show that these diaphragms of the invention exhibit acceptable leak rate (which increases over time) and valve delivery variability when used with the indicated formulations. Little difference is seen between valve stem types or between injection molded diaphragms and compression molded diaphragms. A similar increase in leak rate was observed over time when compression molded FLEXOMER™ DFDA 1138 NT polyolefin was used as the diaphragm material with formulations A4 and B3.

Diaphragms of the invention were prepared from FLEXOMER™ DFDA 1163 NT7 polyolefin and tested with the formulations indicated in TABLE 10 below.

TABLE 10

COMPRESSION MOLDED FLEXOMER™ DFDA 1163 NT 7 POLYOLEFIN

| Formulation | ID | Stem | Time (Weeks) | N | Leak Rate (mg/yr) | Valve Delivery (mg/actuation) |
|---|---|---|---|---|---|---|
| A1 | 80 | ss | 0 | 14 | — | 60.09 ± 0.81 |
|  |  |  | 6 |  | 259 ± 9 | 60.31 ± 0.68 |
|  | 85 | ss | 0 | 14 | — | 60.28 ± 0.78 |
|  |  |  | 6 |  | 279 ± 14 | 60.46 ± 0.86 |
|  | 90 | ss | 0 | 14 | — | 60.31 ± 1.20 |
|  |  |  | 6 |  | 278 ± 17 | 60.56 ± 0.90 |
|  | 95 | ss | 0 | 14 | — | 59.44 ± 1.33 |
|  |  |  | 6 |  | 299 ± 20 | 60.18 ± 0.94 |
|  | 100 | ss | 0 | 14 | — | 59.64 ± 1.35 |
|  |  |  | 6 |  | 394 ± 341 | 60.09 ± 1.15 |
|  | 105 | ss | 0 | 14 | — | 60.01 ± 0.85 |
|  |  |  | 6 |  | 293 ± 22 | 59.79 ± 0.76 |
|  | 80 | pl | 0 | 14 | — | 58.96 ± 0.61 |
|  |  |  | 6 |  | 286 ± 72 | not measured |
|  | 85 | pl | 0 | 14 | — | 59.44 ± 0.56 |
|  |  |  | 6 |  | 275 ± 13 | 58.07 ± 1.80 |
|  | 90 | pl | 0 | 14 | — | 59.22 ± 0.65 |
|  |  |  | 6 |  | 295 ± 45 | 58.51 ± 0.57 |
|  | 95 | pl | 0 | 14 | — | 58.96 ± 0.65 |
|  |  |  | 6 |  | 300 ± 23 | 58.34 ± 0.76 |
|  | 100 | pl | 0 | 14 | — | 58.73 ± 0.70 |
|  |  |  | 6 |  | 315 ± 34 | 58.73 ± 2.18 |
|  | 105 | pl | 0 | 14 | — | 58.19 ± 0.67 |
|  |  |  | 6 |  | 899 ± 2183 | 58.08 ± 1.43 |

The results in TABLE 10 show that these diaphragms of the invention exhibit higher but generally acceptable leak rates and valve delivery variability when used with the indicated formulations, regardless of valve stem type. However, increasing inside diameter appears to increase leak rate with the plastic valve stem.

Diaphragms of the invention were prepared from FLEXOMER™ DFDA 1164 NT7 polyolefin and tested with the formulations indicated in TABLES 11–13 below.

TABLE 11

COMPRESSION MOLDED FLEXOMER™ DFDA 1164 NT 7 POLYOLEFIN

| Formulation | ID | Stem | Time (Weeks) | N | Leak Rate (mg/yr) | Valve Delivery (mg/actuation) |
|---|---|---|---|---|---|---|
| A1 | 80 | ss | 0 | 24 | — | 60.57 ± 0.62 |
|  |  |  | 6 |  | 421 ± 195 | 60.74 ± 0.56 |
|  | 85 | ss | 0 | 14 | — | 61.04 ± 0.99 |
|  |  |  | 6 |  | 338 ± 108 | 61.30 ± 0.88 |
|  | 90 | ss | 0 | 14 | — | 61.16 ± 0.77 |
|  |  |  | 6 |  | 357 ± 264 | 58.94 ± 7.77 |
|  | 95 | ss | 0 | 14 | — | 61.26 ± 0.73 |
|  |  |  | 6 |  | 628 ± 634 | 61.74 ± 0.80 |
|  | 100 | ss | 0 | 14 | — | 60.19 ± 0.65 |
|  |  |  | 6 |  | 458 ± 229 | 60.93 ± 0.90 |
|  | 105 | ss | 0 | 14 | — | 60.60 ± 0.52 |
|  |  |  | 6 |  | 478 ± 263 | 60.90 ± 0.67 |
|  | 80 | pl | 0 | 14 | — | 59.82 ± 0.92 |
|  |  |  | 6 |  | 276 ± 50 | 59.23 ± 0.71 |
|  | 85 | pl | 0 | 14 | — | 59.90 ± 0.78 |
|  |  |  | 6 |  | 264 ± 19 | 59.44 ± 0.75 |
|  | 90 | pl | 0 | 14 | — | 60.02 ± 1.04 |
|  |  |  | 6 |  | 262 ± 16 | 59.64 ± 1.63 |
|  | 95 | pl | 0 | 14 | — | 60.20 ± 1.05 |
|  |  |  | 6 |  | 268 ± 17 | 59.76 ± 1.38 |
|  | 100 | pl | 0 | 14 | — | 58.68 ± 1.74 |
|  |  |  | 6 |  | 380 ± 385 | 58.69 ± 2.87 |
|  | 105 | pl | 0 | 14 | — | 58.41 ± 1.94 |
|  |  |  | 6 |  | 308 ± 48 | 59.73 ± 1.84 |

TABLE 12

INJECTION MOLDED FLEXOMER™ DFDA 1164 NT 7 POLYOLEFIN

| Formulation | ID | Stem | Time (Weeks) | N | Leak Rate (mg/yr) | Valve Delivery (mg/actuation) |
|---|---|---|---|---|---|---|
| A1 | 84 | ss | 0 | 10 | — | 62.34 ± 2.83 |
|  |  |  | 6 |  | 305 ± 35 | 69.99 ± 7.80 |
|  | 88 | ss | 0 | 10 | — | 63.45 ± 4.87 |
|  |  |  | 6 |  | 301 ± 23 | 69.30 ± 9.12 |
|  | 94 | ss | 0 | 10 | — | 65.22 ± 6.21 |
|  |  |  | 6 |  | 304 ± 14 | 69.09 ± 7.02 |

TABLE 12-continued

INJECTION MOLDED FLEXOMER™ DFDA 1164 NT 7 POLYOLEFIN

| Formulation | ID | Stem | Time (Weeks) | N | Leak Rate (mg/yr) | Valve Delivery (mg/actuation) |
|---|---|---|---|---|---|---|
| | 99 | ss | 0 | 10 | — | 65.51 ± 5.42 |
| | | | 6 | | 308 ± 19 | 81.53 ± 25.99 |
| | 84 | pl | 0 | 10 | — | 62.62 ± 2.15 |
| | | | 6 | | 428 ± 334 | 60.99 ± 4.02 |
| | 88 | pl | 0 | 10 | — | 60.67 ± 2.76 |
| | | | 6 | | 350 ± 110 | 59.67 ± 3.38 |
| | 94 | pl | 0 | 10 | — | 64.18 ± 5.65 |
| | | | 6 | | 582 ± 397 | 60.67 ± 2.30 |
| | 99 | pl | 0 | 10 | — | 62.19 ± 3.86 |
| | | | 6 | | 327 ± 23 | not measured |
| B1 | 84 | ss | 0 | 10 | — | 69.83 ± 6.84 |
| | | | 6 | | 284 ± 22 | 76.36 ± 8.94 |
| | 88 | ss | 0 | 10 | — | 70.33 ± 5.42 |
| | | | 6 | | 260 ± 33 | 74.86 ± 6.29 |
| | 94 | ss | 0 | 10 | — | 67.83 ± 4.70 |
| | | | 6 | | 273 ± 33 | 71.89 ± 4.32 |
| | 99 | ss | 0 | 10 | — | 69.73 ± 4.97 |
| | | | 6 | | 255 ± 19 | 81.76 ± 8.71 |
| B1 | 84 | pl | 0 | 10 | — | 69.04 ± 5.87 |
| | | | 6 | | 286 ± 29 | 69.72 ± 6.85 |
| | 88 | pl | 0 | 10 | — | 68.16 ± 6.78 |
| | | | 6 | | 629 ± 1064 | 69.30 ± 6.70 |
| | 94 | pl | 0 | 10 | — | 66.15 ± 2.89 |
| | | | 6 | | 292 ± 38 | 67.20 ± 8.22 |
| | 99 | pl | 0 | 10 | — | 69.45 ± 7.39 |
| | | | 6 | | 491 ± 654 | 70.29 ± 7.77 |

TABLE 13

EXTRUDED FLEXOMER™ DFDA 1164 NT 7 POLYOLEFIN

| Formulation | ID | Stem | Time (Weeks) | N | Leak Rate (mg/yr) | Valve Delivery (mg/actuation) |
|---|---|---|---|---|---|---|
| B2 | 80 | ss | 0 | 10 | — | 66.90 ± 0.37 |
| | | | 6 | | 306 ± 154 | 67.05 ± 0.42 |
| | 85 | ss | 0 | 10 | — | 65.26 ± 1.26 |
| | | | 6 | | 321 ± 271 | 63.81 ± 1.61 |
| | 90 | ss | 0 | 10 | — | 65.10 ± 0.96 |
| | | | 6 | | 232 ± 122 | 66.55 ± 0.76 |
| | 95 | ss | 0 | 10 | — | 65.67 ± 1.30 |
| | | | 6 | | 425 ± 292 | 66.53 ± 0.90 |
| | 100 | ss | 0 | 10 | — | 66.58 ± 2.91 |
| | | | 6 | | 757 ± 380 | 66.39 ± 1.54 |
| | 105 | ss | 0 | 10 | — | 65.03 ± 2.90 |
| | | | 6 | | 698 ± 499 | 67.02 ± 1.61 |
| | 80 | pl | 0 | 10 | — | 64.77 ± 2.20 |
| | | | 6 | | 184 ± 29 | 64.29 ± 1.45 |
| | 85 | pl | 0 | 10 | — | 63.55 ± 1.17 |
| | | | 6 | | 211 ± 23 | 63.53 ± 1.07 |
| | 90 | pl | 0 | 10 | — | 63.40 ± 0.57 |
| | | | 6 | | 198 ± 21 | 64.45 ± 1.60 |
| | 95 | pl | 0 | 10 | — | 63.43 ± 0.63 |
| | | | 6 | | 226 ± 24 | 64.70 ± 1.85 |
| | 100 | pl | 0 | 10 | — | 63.59 ± 0.71 |
| | | | 6 | | 341 ± 388 | 66.27 ± 4.49 |
| | 105 | pl | 0 | 10 | — | 63.17 ± 0.85 |
| | | | 6 | | 226 ± 29 | 69.72 ± 8.48 |

The results in TABLES 11–13 show that these diaphragms of the invention exhibit higher but generally suitable leak rate and valve delivery variability when used with the indicated formulations. Valve delivery is least variable for the compression molded diaphragms. With the extruded diaphragms leak rate with the beclomethasone dipropionate formulation is improved when a plastic valve stem is used.

Diaphragms of the invention were prepared from FLEXOMER™ DEFD 1491 NT7 polyolefin and tested with the formulations indicated in TABLE 14 below.

TABLE 14

COMPRESSION MOLDED FLEXOMER™ DEFD 1491 NT 7 POLYOLEFIN

| Formulation | ID | Stem | Time (Weeks) | N | Leak Rate (mg/yr) | Valve Delivery (mg/actuation) |
|---|---|---|---|---|---|---|
| A1 | 80 | ss | 0 | 14 | — | 58.69 ± 1.15 |
| | | | 6 | | 275 ± 26 | 58.86 ± 1.46 |
| | 85 | ss | 0 | 14 | — | 59.00 ± 0.83 |
| | | | 6 | | 277 ± 23 | 59.42 ± 0.75 |
| | 90 | ss | 0 | 14 | — | 59.13 ± 0.97 |
| | | | 6 | | 268 ± 20 | 59.59 ± 0.96 |
| | 95 | ss | 0 | 14 | — | 58.95 ± 0.91 |
| | | | 6 | | 284 ± 26 | 59.50 ± 0.79 |
| | 100 | ss | 0 | 14 | — | 59.07 ± 0.79 |
| | | | 6 | | 279 ± 19 | 59.04 ± 1.08 |
| | 105 | ss | 0 | 14 | — | 59.06 ± 0.53 |
| | | | 6 | | 272 ± 18 | 59.51 ± 1.18 |
| | 80 | pl | 0 | 14 | — | 57.39 ± 2.06 |
| | | | 6 | | 267 ± 10 | 57.33 ± 1.33 |
| | 85 | pl | 0 | 14 | — | 58.22 ± 0.54 |
| | | | 6 | | 283 ± 28 | 57.66 ± 0.64 |
| | 90 | pl | 0 | 14 | — | 58.35 ± 0.69 |
| | | | 6 | | 269 ± 8 | 56.83 ± 3.43 |
| | 95 | pl | 0 | 14 | — | 58.02 ± 0.84 |
| | | | 6 | | 276 ± 13 | 57.68 ± 0.58 |
| | 100 | pl | 0 | 14 | — | 57.72 ± 0.74 |
| | | | 6 | | 281 ± 17 | 57.26 ± 0.88 |
| | 105 | pl | 0 | 14 | — | 58.29 ± 0.65 |
| | | | 6 | | 276 ± 19 | 56.21 ± 3.22 |

The results in TABLE 14 show that these diaphragms of the invention exhibit acceptable leak rates and valve delivery variability when used with the indicated formulations.

Diaphragms of the invention were prepared from FLEXOMER™ DFDA 9020 NT7 polyolefin and tested with the formulations indicated in TABLES 15–16.

TABLE 15

EXTRUDED FLEXOMER™ DFDA 9020 NT 7 POLYOLEFIN

| Formulation | ID | Stem | Time (Weeks) | N | Leak Rate (mg/yr) | Valve Delivery (mg/actuation) |
|---|---|---|---|---|---|---|
| A2 | 80 | ss | 0 | 14 | — | 58.82 ± 3.64 |
| | | | 6 | | 262 ± 14 | 59.68 ± 0.77 |
| | 85 | ss | 0 | 14 | — | 59.57 ± 1 24 |
| | | | 6 | | 278 ± 22 | 59.71 ± 0.84 |
| | 90 | ss | 0 | 14 | — | 59.54 ± 0.73 |
| | | | 6 | | 271 ± 20 | 59.46 ± 0.41 |
| | 95 | ss | 0 | 14 | — | 59.91 ± 1.15 |
| | | | 6 | | 296 ± 22 | 59.51 ± 0.64 |
| | 100 | ss | 0 | 14 | — | 60.09 ± 0.84 |
| | | | 6 | | 289 ± 17 | 60.83 ± 4.08 |
| | 105 | ss | 0 | 14 | — | 59.99 ± 1.31 |
| | | | 6 | | 283 ± 15 | 60.04 ± 0.92 |
| | 80 | pl | 0 | 14 | — | 57.99 ± 1.83 |
| | | | 6 | | 281 ± 41 | 57.30 ± 2.62 |
| | 85 | pl | 0 | 14 | — | 58.18 ± 0.89 |
| | | | 6 | | 302 ± 20 | 57.77 ± 0.63 |
| | 90 | pl | 0 | 14 | — | 59.11 ± 0.69 |
| | | | 6 | | 291 ± 21 | 58.42 ± 0.68 |
| | 95 | pl | 0 | 14 | — | 58.54 ± 0.80 |
| | | | 6 | | 354 ± 103 | 57.79 ± 0.63 |
| | 100 | pl | 0 | 14 | — | 58.59 ± 1.09 |
| | | | 6 | | 319 ± 16 | 58.58 ± 2.84 |
| | 105 | pl | 0 | 14 | — | 58.20 ± 0.74 |
| | | | 6 | | 319 ± 30 | 57.99 ± 1.23 |

TABLE 16

COMPRESSION MOLDED FLEXOMER ™ DFDA 9020 NT 7 POLYOLEFIN

| Formulation | ID | Stem | Time (Weeks) | N | Leak Rate (mg/yr) | Valve Delivery (mg/actuation) |
|---|---|---|---|---|---|---|
| A3 | 80 | pl | 0 | 14 | — | 59.43 ± 0.70 |
|  |  |  | 6 |  | not measured | 58.82 ± 0.74 |
|  | 85 | pl | 0 | 14 | — | 59.27 ± 0.78 |
|  |  |  | 6 |  | 240 ± 15 | 58.76 ± 0.41 |
|  | 90 | pl | 0 | 14 | — | 59.44 ± 2.03 |
|  |  |  | 6 |  | 230 ± 18 | 58.67 ± 0.83 |
|  | 95 | pl | 0 | 14 | — | 59.09 ± 0.73 |
|  |  |  | 6 |  | 236 ± 17 | 58.95 ± 0.79 |
|  | 100 | pl | 0 | 14 | — | 58.51 ± 2.49 |
|  |  |  | 6 |  | 243 ± 76 | 58.06 ± 2.04 |
|  | 105 | pl | 0 | 14 | — | 59.00 ± 1.27 |
|  |  |  | 6 |  | 304 ± 253 | 58.63 ± 1.98 |
| B2 | 80 | ss | 0 | 14 | — | 65.57 ± 1.14 |
|  |  |  | 6 |  | 221 ± 90 | 66.66 ± 0.86 |
|  | 85 | ss | 0 | 14 | — | 65.75 ± 0.80 |
|  |  |  | 6 |  | 338 ± 228 | 66.67 ± 1.42 |
|  | 90 | ss | 0 | 14 | — | 65.56 ± 1.30 |
|  |  |  | 6 |  | 471 ± 482 | 66.74 ± 0.80 |
|  | 95 | ss | 0 | 14 | — | 66.35 ± 2.19 |
|  |  |  | 6 |  | 424 ± 381 | 67.03 ± 0.93 |
|  | 100 | ss | 0 | 14 | — | 65.72 ± 0.67 |
|  |  |  | 6 |  | 564 ± 490 | 66.40 ± 0.60 |
|  | 105 | ss | 0 | 14 | — | 66.40 ± 1.32 |
|  |  |  | 6 |  | 671 ± 622 | 66.43 ± 1.14 |
| B2 | 80 | pl | 0 | 14 | — | 63.26 ± 0.48 |
|  |  |  | 6 |  | 174 ± 18 | 63.41 ± 0.50 |
|  | 85 | pl | 0 | 14 | — | 62.93 ± 0.86 |
|  |  |  | 6 |  | 186 ± 21 | 63.80 ± 0.78 |
|  | 90 | pl | 0 | 14 | — | 63.50 ± 0.97 |
|  |  |  | 6 |  | 179 ± 13 | 64.24 ± 0.89 |
|  | 95 | pl | 0 | 14 | — | 62.82 ± 1.71 |
|  |  |  | 6 |  | 175 ± 10 | 64.58 ± 1.13 |
|  | 100 | pl | 0 | 14 | — | 62.60 ± 2.83 |
|  |  |  | 6 |  | 174 ± 33 | 63.43 ± 1.69 |
|  | 105 | pl | 0 | 14 | — | 63.51 ± 1.47 |
|  |  |  | 6 |  | 168 ± 18 | 66.57 ± 8.55 |

The results in TABLES 15 and 16 show that the extruded and compression molded diaphragms have valve delivery and leak rate especially suitable for use with a polar ionized drug (albuterol sulfate), while the compression molded diaphragms used with the plastic valve stem are particularly suitable for use with a steroid formulation (beclomethasone dipropionate).

Diaphragms of the invention were prepared from FLEXOMER™ DEFD 9042 NT polyolefin and tested with the formulations indicated in TABLES 17–19 below.

TABLE 17

COMPRESSION MOLDED FLEXOMER ™ 9042 NT POLYOLEFIN

| Formulation | ID | Stem | Time (Weeks) | N | Leak Rate (mg/yr) | Valve Delivery (mg/actuation) |
|---|---|---|---|---|---|---|
| A1 | 80 | ss | 0 | 14 | — | 61.59 ± 1.50 |
|  |  |  | 3 |  | 270 ± 20 | 63.14 ± 0.88 |
|  | 85 | ss | 0 | 14 | — | 60.77 ± 2.30 |
|  |  |  | 6 |  | 249 ± 22 | 63.18 ± 1.04 |
|  | 90 | ss | 0 | 14 | — | 58.94 ± 4.45 |
|  |  |  | 6 |  | 252 ± 19 | 60.86 ± 2.81 |
|  | 95 | ss | 0 | 14 | — | 59.81 ± 2.42 |
|  |  |  | 6 |  | 251 ± 21 | 60.46 ± 2.22 |
|  | 100 | ss | 0 | 14 | — | 44.61 ± 13.56 |
|  |  |  | 6 |  | 270 ± 33 | 50.75 ± 5.58 |
|  | 105 | ss | 0 | 14 | — | 58.16 ± 1.23 |
|  |  |  | 6 |  | 187 ± 25 | 59.01 ± 0.82 |
|  | 80 | pl | 0 | 14 | — | 61.14 ± 0.59 |

TABLE 17-continued

COMPRESSION MOLDED FLEXOMER ™ 9042 NT POLYOLEFIN

| Formulation | ID | Stem | Time (Weeks) | N | Leak Rate (mg/yr) | Valve Delivery (mg/actuation) |
|---|---|---|---|---|---|---|
|  |  |  | 6 |  | 268 ± 22 | 61.29 ± 0.66 |
|  | 85 | pl | 0 | 14 | — | 59.96 ± 1.28 |
|  |  |  | 6 |  | 265 ± 14 | 60.41 ± 0.88 |
|  | 90 | pl | 0 | 14 | — | 57.35 ± 1.68 |
|  |  |  | 6 |  | 339 ± 141 | 55.71 ± 5.71 |
|  | 95 | pl | 0 | 14 | — | 54.95 ± 2.84 |
|  |  |  | 6 |  | 286 ± 30 | 55.44 ± 3.48 |
|  | 100 | pl | 0 | 14 | — | 55.37 ± 4.10 |
|  |  |  | 6 |  | 304 ± 24 | 56.25 ± 3.33 |
|  | 105 | pl | 0 | 14 | — | 57.83 ± 0.67 |
|  |  |  | 6 |  | 208 ± 31 | 60.14 ± 2.62 |

TABLE 18

EXTRUDED FLEXOMER ™ DEFD 9042 NT POLYOLEFIN

| Formulation | ID | Stem | Time (Weeks) | N | Leak Rate (mg/yr) | Valve Delivery (mg/actuation) |
|---|---|---|---|---|---|---|
| A2 | 80 | ss | 0 | 14 | — | 61.21 ± 1.86 |
|  |  |  | 6 |  | 289 ± 85 | 61.10 ± 1.26 |
|  | 85 | ss | 0 | 14 | — | 60.89 ± 1.62 |
|  |  |  | 6 |  | 281 ± 63 | 60.50 ± 3.44 |
|  | 90 | ss | 0 | 14 | — | 61.18 ± 2.86 |
|  |  |  | 6 |  | 294 ± 64 | 60.65 ± 1.09 |
|  | 95 | ss | 0 | 14 | — | 58.47 ± 1.01 |
|  |  |  | 6 |  | 252 ± 18 | 60.59 ± 1.20 |
|  | 100 | ss | 0 | 14 | — | 59.40 ± 1.27 |
|  |  |  | 6 |  | 255 ± 12 | 60.35 ± 1.16 |
|  | 105 | ss | 0 | 14 | — | 59.94 ± 1.22 |
|  |  |  | 6 |  | 437 ± 375 | 60.97 ± 0.69 |
|  | 80 | pl | 0 | 14 | — | 57.99 ± 0.72 |
|  |  |  | 6 |  | 246 ± 9 | 57.71 ± 0.52 |
|  | 85 | pl | 0 | 14 | — | 58.12 ± 0.98 |
|  |  |  | 6 |  | 262 ± 10 | 53.93 ± 15.53 |
|  | 90 | pl | 0 | 14 | — | 57.88 ± 0.85 |
|  |  |  | 6 |  | 262 ± 16 | 57.40 ± 1.79 |
|  | 95 | pl | 0 | 14 | — | 58.15 ± 1.10 |
|  |  |  | 6 |  | 256 ± 14 | 57.88 ± 1.44 |
|  | 100 | pl | 0 | 14 | — | 57.06 ± 1.40 |
|  |  |  | 6 |  | 268 ± 26 | 57.31 ± 0.79 |
|  | 105 | pl | 0 | 14 | — | 56.21 ± 1.68 |
|  |  |  | 6 |  | 316 ± 94 | 59.84 ± 6.31 |

TABLE 19

INJECTION MOLDED FLEXOMER ™ DEFD 9042 NT POLYOLEFIN

| Formulation | ID | Stem | Time (Weeks) | N | Leak Rate (mg/yr) | Valve Delivery (mg/actuation) |
|---|---|---|---|---|---|---|
| A2 | 84 | ss | 0 | 10 | — | 60.40 ± 1.70 |
|  |  |  | 6 |  | 282 ± 13 | 67.20 ± 8.78 |
|  | 88 | ss | 0 | 10 | — | 60.40 ± 1.28 |
|  |  |  | 6 |  | 282 ± 13 | 75.56 ± 25.41 |
|  | 94 | ss | 0 | 10 | — | 61.60 ± 2.07 |
|  |  |  | 6 |  | 282 ± 14 | 66.63 ± 13.64 |
|  | 99 | ss | 0 | 10 | — | 60.83 ± 2.18 |
|  |  |  | 6 |  | 297 ± 16 | 62.80 ± 3.61 |
|  | 84 | pl | 0 | 10 | — | 59.00 ± 1.82 |
|  |  |  | 6 |  | 272 ± 14 | 61.30 ± 8.54 |
|  | 88 | pl | 0 | 10 | — | 65.99 ± 12.41 |
|  |  |  | 6 |  | 286 ± 22 | 60.32 ± 4.43 |
|  | 94 | pl | 0 | 10 | — | 61.20 ± 3.64 |
|  |  |  | 6 |  | 284 ± 18 | 60.28 ± 3.42 |
|  | 99 | pl | 0 | 10 | — | 61.22 ± 4.87 |
|  |  |  | 6 |  | 291 ± 8 | 59.40 ± 3.19 |
| B2 | 84 | ss | 0 | 10 | — | 70.48 ± 10.53 |
|  |  |  | 6 |  | 198 ± 11 | 69.54 ± 3.92 |

TABLE 19-continued

INJECTION MOLDED FLEXOMER ™ DEFD 9042 NT POLYOLEFIN

| Formulation | ID | Stem | Time (Weeks) | N | Leak Rate (mg/yr) | Valve Delivery (mg/actuation) |
|---|---|---|---|---|---|---|
| | 88 | ss | 0 | 10 | — | 64.71 ± 1.23 |
| | | | 6 | | 202 ± 18 | 71.80 ± 7.10 |
| | 94 | ss | 0 | 10 | — | 65.01 ± 2.66 |
| | | | 6 | | 199 ± 18 | 86.26 ± 31.64 |
| | 99 | ss | 0 | 10 | — | 66.80 ± 5.98 |
| | | | 6 | | 208 ± 30 | 80.90 ± 34.78 |
| B2 | 84 | pl | 0 | 10 | — | 64.81 ± 3.57 |
| | | | 6 | | 207 ± 15 | 63.90 ± 1.47 |
| | 88 | p1 | 0 | 10 | — | 63.96 ± 4.78 |
| | | | 6 | | 200 ± 10 | 64.46 ± 2.31 |
| | 94 | pl | 0 | 10 | — | 65.17 ± 4.19 |
| | | | 6 | | 207 ± 14 | 69.00 ± 7.64 |
| | 99 | pl | 0 | 10 | — | 65.27 ± 3.27 |
| | | | 6 | | 219 ± 22 | 78.26 ± 40.98 |

The results in TABLES 17–19 show that in this instance compression molded and extruded diaphragms generally perform better than the injection molded diaphragms with these formulations.

Diaphragms of the invention were prepared from polymer blends of the invention as set forth in TABLES 20–25 (parts and percentages are by weight) and tested with the formulations indicated in said TABLES.

TABLE 20

COMPRESSION MOLDED POLYMER BLEND.
DFDA 1137 NT 7/GERS 1085 NT (25/75)

| Formulation | ID | Stem | Time (Weeks) | N | Leak Rate (mg/yr) | Valve Delivery (mg/actuation) |
|---|---|---|---|---|---|---|
| A1 | 80 | ss | 0 | 10 | — | 55.70 ± 1.91 |
| | | | 6 | | 271 ± 18 | 56.55 ± 0.62 |
| | 85 | ss | 0 | 10 | — | 54.38 ± 6.57 |
| | | | 6 | | 261 ± 12 | 57.31 ± 0.88 |
| | 90 | ss | 0 | 10 | — | 56.08 ± 1.96 |
| | | | 6 | | 264 ± 10 | 57.22 ± 0.96 |
| | 95 | ss | 0 | 10 | — | 56.00 ± 1.08 |
| | | | 6 | | 264 ± 15 | 56.97 ± 1.09 |
| | 100 | ss | 0 | 10 | — | 55.54 ± 1.03 |
| | | | 6 | | 266 ± 12 | 56.91 ± 0.84 |
| | 105 | ss | 0 | 10 | — | 56.45 ± 0.89 |
| | | | 6 | | 278 ± 19 | 57.49 ± 0.62 |
| | 80 | pl | 0 | 10 | — | 54.29 ± 1.45 |
| | | | 6 | | 259 ± 12 | 54.81 ± 0.41 |
| | 85 | pl | 0 | 10 | — | 54.93 ± 0.89 |
| | | | 6 | | 271 ± 18 | 55.79 ± 0.71 |
| | 90 | pl | 0 | 10 | — | 55.63 ± 0.89 |
| | | | 6 | | 264 ± 7 | 55.39 ± 0.60 |
| | 95 | pl | 0 | 10 | — | 55.43 ± 1.02 |
| | | | 6 | | 271 ± 13 | 55.34 ± 1.32 |
| | 100 | pl | 0 | 10 | — | 55.56 ± 0.47 |
| | | | 6 | | 283 ± 24 | 55.70 ± 0.88 |
| | 105 | pl | 0 | 10 | — | 55.75 ± 0.75 |
| | | | 6 | | 280 ± 17 | 56.17 ± 1.06 |
| B1 | 80 | ss | 0 | 10 | — | 60.45 ± 0.85 |
| | | | 6 | | 234 ± 12 | 61.10 ± 0.80 |
| | 85 | ss | 0 | 10 | — | 59.99 ± 1.88 |
| | | | 6 | | 224 ± 16 | 62.23 ± 0.92 |
| | 90 | ss | 0 | 10 | — | 60.23 ± 0.74 |
| | | | 6 | | 232 ± 17 | 61.52 ± 0.54 |
| | 95 | ss | 0 | 10 | — | 60.27 ± 0.95 |
| | | | 6 | | 242 ± 28 | 61.37 ± 0.58 |
| | 100 | ss | 0 | 10 | — | 60.77 ± 0.59 |
| | | | 6 | | 230 ± 17 | 61.65 ± 0.62 |
| | 105 | ss | 0 | 10 | — | 60.56 ± 0.87 |
| | | | 6 | | 240 ± 17 | 63.19 ± 3.70 |
| | 80 | pl | 0 | 10 | — | 59.08 ± 0.64 |
| | | | 6 | | 222 ± 22 | 59.35 ± 0.46 |

TABLE 20-continued

COMPRESSION MOLDED POLYMER BLEND.
DFDA 1137 NT 7/GERS 1085 NT (25/75)

| Formulation | ID | Stem | Time (Weeks) | N | Leak Rate (mg/yr) | Valve Delivery (mg/actuation) |
|---|---|---|---|---|---|---|
| | 85 | pl | 0 | 10 | — | 58.83 ± 2.94 |
| | | | 6 | | 236 ± 22 | 60.18 ± 0.87 |
| | 90 | pl | 0 | 10 | — | 59.55 ± 0.79 |
| | | | 6 | | 234 ± 20 | 60.05 ± 1.17 |
| | 95 | pl | 0 | 10 | — | 59.14 ± 1.68 |
| | | | 6 | | 255 ± 24 | 59.80 ± 2.01 |
| | 100 | pl | 0 | 10 | — | 59.91 ± 0.48 |
| | | | 6 | | 249 ± 20 | 60.39 ± 1.38 |
| | 105 | pl | 0 | 10 | — | 59.32 ± 0.61 |
| | | | 6 | | 249 ± 16 | 60.00 ± 0.37 |

TABLE 21

COMPRESSION MOLDED POLYMER BLEND.
DFDA 1137 NT 7/GERS 1085 NT (50/50)

| Formulation | ID | Stem | Time (Weeks) | N | Leak Rate (mg/yr) | Valve Delivery (mg/actuation) |
|---|---|---|---|---|---|---|
| A1 | 80 | ss | 0 | 10 | — | 57.35 ± 1.07 |
| | | | 6 | | 267 ± 15 | 58.50 ± 0.54 |
| | 85 | ss | 0 | 10 | — | 56.97 ± 0.64 |
| | | | 6 | | 273 ± 14 | 57.92 ± 0.64 |
| | 90 | ss | 0 | 10 | — | 56.87 ± 0.87 |
| | | | 6 | | 279 ± 24 | 57.99 ± 0.74 |
| | 95 | ss | 0 | 10 | — | 57.65 ± 1.16 |
| | | | 6 | | 267 ± 10 | 58.46 ± 0.89 |
| | 100 | ss | 0 | 10 | — | 57.17 ± 1.06 |
| | | | 6 | | 265 ± 16 | 57.98 ± 0.85 |
| | 105 | ss | 0 | 10 | — | 57.83 ± 1.10 |
| | | | 6 | | 266 ± 11 | 58.77 ± 0.88 |
| | 80 | pl | 0 | 10 | — | 56.73 ± 0.66 |
| | | | 6 | | 284 ± 17 | 55.55 ± 3.81 |
| | 85 | pl | 0 | 10 | — | 56.13 ± 1.85 |
| | | | 6 | | 282 ± 23 | 56.23 ± 0.77 |
| | 90 | pl | 0 | 10 | — | 56.87 ± 0.59 |
| | | | 6 | | 267 ± 9 | 56.41 ± 0.99 |
| | 95 | pl | 0 | 10 | — | 56.69 ± 0.73 |
| | | | 6 | | 285 ± 29 | 57.21 ± 0.38 |
| | 100 | pl | 0 | 10 | — | 55.28 ± 3.52 |
| | | | 6 | | 269 ± 8 | 56.98 ± 0.55 |
| | 105 | pl | 0 | 10 | — | 57.15 ± 0.41 |
| | | | 6 | | 271 ± 12 | 57.06 ± 0.62 |
| B1 | 80 | ss | 0 | 10 | — | 61.83 ± 0.93 |
| | | | 6 | | 206 ± 9 | 63.37 ± 0.87 |
| | 85 | ss | 0 | 10 | — | 60.98 ± 0.78 |
| | | | 6 | | 206 ± 17 | 62.90 ± 0.99 |
| | 90 | ss | 0 | 10 | — | 61.80 ± 0.85 |
| | | | 6 | | 196 ± 11 | 63.12 ± 0.94 |
| | 95 | ss | 0 | 10 | — | 61.94 ± 1.11 |
| | | | 6 | | 205 ± 11 | 63.26 ± 0.86 |
| | 100 | ss | 0 | 10 | — | 61.94 ± 0.95 |
| | | | 6 | | 201 ± 13 | 62.99 ± 0.97 |
| | 105 | ss | 0 | 10 | — | 62.61 ± 0.96 |
| | | | 6 | | 192 ± 12 | 63.70 ± 0.78 |
| | 80 | pl | 0 | 10 | — | 60.39 ± 0.60 |
| | | | 6 | | 210 ± 19 | 61.08 ± 0.71 |
| | 85 | pl | 0 | 10 | — | 59.80 ± 0.38 |
| | | | 6 | | 211 ± 11 | 61.44 ± 1.31 |
| | 90 | pl | 0 | 10 | — | 61.52 ± 0.58 |
| | | | 6 | | 202 ± 10 | 61.89 ± 0.63 |
| | 95 | pl | 0 | 10 | — | 55.62 ± 17.44 |
| | | | 6 | | 193 ± 8 | 61.96 ± 0.94 |
| | 100 | pl | 0 | 10 | — | 61.30 ± 0.52 |
| | | | 6 | | 202 ± 13 | 62.18 ± 0.56 |
| | 105 | pl | 0 | 10 | — | 61.53 ± 0.86 |
| | | | 6 | | 203 ± 15 | 61.68 ± 0.75 |

TABLE 22

COMPRESSION MOLDED POLYMER BLEND.
DFDA 1137 NT 7/GERS 1085 NT (75/25)

| Formulation | ID | Stem | Time (Weeks) | N | Leak Rate (mg/yr) | Valve Delivery (mg/actuation) |
|---|---|---|---|---|---|---|
| A1 | 80 | ss | 0 | 10 | — | 57.92 ± 1.25 |
|  |  |  | 6 |  | 374 ± 24 | 58.18 ± 0.84 |
|  | 85 | ss | 0 | 10 | — | 58.31 ± 0.90 |
|  |  |  | 6 |  | 385 ± 27 | 58.85 ± 0.80 |
|  | 90 | ss | 0 | 10 | — | 58.01 ± 0.58 |
|  |  |  | 6 |  | 332 ± 16 | 58.85 ± 0.80 |
|  | 95 | ss | 0 | 10 | — | 57.93 ± 0.84 |
|  |  |  | 6 |  | 314 ± 28 | 58.86 ± 0.77 |
|  | 100 | ss | 0 | 10 | — | 57.23 ± 1.01 |
|  |  |  | 6 |  | 294 ± 16 | 58.20 ± 0.94 |
|  | 105 | ss | 0 | 10 | — | 58.07 ± 1.13 |
|  |  |  | 6 |  | 324 ± 19 | 58.61 ± 1.07 |
|  | 80 | pl | 0 | 10 | — | 57.07 ± 1.02 |
|  |  |  | 6 |  | 392 ± 20 | 57.31 ± 0.62 |
|  | 85 | pl | 0 | 10 | — | 57.39 ± 0.39 |
|  |  |  | 6 |  | 380 ± 41 | 57.83 ± 0.53 |
|  | 90 | pl | 0 | 10 | — | 57.14 ± 0.51 |
|  |  |  | 6 |  | 340 ± 27 | 57.45 ± 0.81 |
|  | 95 | pl | 0 | 10 | — | 57.54 ± 0.50 |
|  |  |  | 6 |  | 299 ± 16 | 57.44 ± 0.57 |
|  | 100 | pl | 0 | 10 | — | 56.95 ± 0.71 |
|  |  |  | 6 |  | 309 ± 13 | 57.38 ± 2.62 |
|  | 105 | pl | 0 | 10 | — | 56.13 ± 1.71 |
|  |  |  | 6 |  | 331 ± 29 | 56.78 ± 0.80 |
| B1 | 80 | ss | 0 | 10 | — | 61.92 ± 0.77 |
|  |  |  | 6 |  | 205 ± 13 | 63.21 ± 0.61 |
|  | 85 | ss | 0 | 10 | — | 61.81 ± 0.52 |
|  |  |  | 6 |  | 201 ± 6 | 63.52 ± 0.57 |
|  | 90 | ss | 0 | 10 | — | 61.80 ± 1.23 |
|  |  |  | 6 |  | 201 ± 11 | 63.63 ± 1.68 |
|  | 95 | ss | 0 | 10 | — | 61.86 ± 0.86 |
|  |  |  | 6 |  | 201 ± 15 | 63.32 ± 0.98 |
|  | 100 | ss | 0 | 10 | — | 62.16 ± 0.94 |
|  |  |  | 6 |  | 209 ± 23 | 63.64 ± 0.97 |
|  | 105 | ss | 0 | 10 | — | 62.46 ± 0.83 |
|  |  |  | 6 |  | 204 ± 11 | 63.39 ± 1.11 |
|  | 80 | pl | 0 | 10 | — | 60.75 ± 0.62 |
|  |  |  | 6 |  | 199 ± 11 | 61.62 ± 0.64 |
|  | 85 | pl | 0 | 10 | — | 60.93 ± 0.50 |
|  |  |  | 6 |  | 212 ± 16 | 62.08 ± 0.72 |
|  | 90 | pl | 0 | 10 | — | 60.44 ± 1.84 |
|  |  |  | 6 |  | 205 ± 14 | 62.48 ± 1.21 |
|  | 95 | pl | 0 | 10 | — | 61.06 ± 0.47 |
|  |  |  | 6 |  | 205 ± 7 | 62.12 ± 0.95 |
|  | 100 | pl | 0 | 10 | — | 60.49 ± 0.68 |
|  |  |  | 6 |  | 210 ± 27 | 61.41 ± 0.67 |
|  | 105 | pl | 0 | 10 | — | 60.54 ± 2.61 |
|  |  |  | 6 |  | 201 ± 13 | 61.96 ± 0.74 |

TABLE 23

COMPRESSION MOLDED POLYMER BLEND.
DFDA 1137 NT 7/GERS 1085 NT/TALC (23.2/69.8/7.0)

| Formulation | ID | Stem | Time (Weeks) | N | Leak Rate (mg/yr) | Valve Delivery (mg/actuation) |
|---|---|---|---|---|---|---|
| A2 | 80 | ss | 0 | 10 | — | 59.26 ± 1.00 |
|  |  |  | 6 |  | 296 ± 37 | 59.82 ± 1.06 |
|  | 85 | ss | 0 | 10 | — | 59.19 ± 0.85 |
|  |  |  | 6 |  | 265 ± 31 | 60.39 ± 0.83 |
|  | 90 | ss | 0 | 10 | — | 60.44 ± 1.07 |
|  |  |  | 6 |  | 278 ± 34 | 62.03 ± 0.70 |
|  | 95 | ss | 0 | 10 | — | 59.71 ± 1.90 |
|  |  |  | 6 |  | 313 ± 43 | 61.78 ± 0.57 |
|  | 100 | ss | 0 | 10 | — | 59.61 ± 0.84 |
|  |  |  | 6 |  | 303 ± 40 | 61.31 ± 0.84 |
|  | 105 | ss | 0 | 10 | — | 59.98 ± 1.21 |
|  |  |  | 6 |  | 311 ± 53 | 61.49 ± 1.06 |
|  | 80 | pl | 0 | 10 | — | 57.71 ± 0.70 |
|  |  |  | 6 |  | 300 ± 48 | 57.54 ± 0.63 |
|  | 85 | pl | 0 | 10 | — | 57.73 ± 0.54 |
|  |  |  | 6 |  | 264 ± 29 | 57.56 ± 0.33 |
|  | 90 | pl | 0 | 10 | — | 58.04 ± 0.78 |
|  |  |  | 6 |  | 287 ± 33 | 58.46 ± 0.64 |
|  | 95 | pl | 0 | 10 | — | 58.24 ± 0.70 |
|  |  |  | 6 |  | 282 ± 22 | 58.79 ± 0.59 |
|  | 100 | pl | 0 | 10 | — | 57.80 ± 0.44 |
|  |  |  | 6 |  | 310 ± 43 | 59.33 ± 1.45 |
|  | 105 | pl | 0 | 10 | — | 58.30 ± 0.61 |
|  |  |  | 6 |  | 366 ± 39 | 59.16 ± 0.44 |
| B2 | 80 | ss | 0 | 10 | — | 61.80 ± 1.00 |
|  |  |  | 6 |  | 194 ± 6 | not measured |
|  | 85 | ss | 0 | 10 | — | 61.94 ± 0.98 |
|  |  |  | 6 |  | 185 ± 16 | 64.04 ± 0.69 |
|  | 90 | ss | 0 | 10 | — | 61.40 ± 2.70 |
|  |  |  | 6 |  | 206 ± 28 | 65.21 ± 0.88 |
|  | 95 | ss | 0 | 10 | — | 62.82 ± 1.03 |
|  |  |  | 6 |  | 196 ± 15 | 65.31 ± 0.81 |
|  | 100 | ss | 0 | 10 | — | 60.04 ± 6.25 |
|  |  |  | 6 |  | 218 ± 35 | 65.37 ± 0.67 |
|  | 105 | ss | 0 | 10 | — | 63.57 ± 1.54 |
|  |  |  | 6 |  | 215 ± 36 | 65.14 ± 0.77 |
|  | 80 | pl | 0 | 10 | — | 60.74 ± 0.73 |
|  |  |  | 6 |  | 221 ± 41 | 61.69 ± 0.65 |
|  | 85 | pl | 0 | 10 | — | 60.69 ± 0.79 |
|  |  |  | 6 |  | 188 ± 7 | 61.99 ± 0.72 |
|  | 90 | pl | 0 | 10 | — | 61.33 ± 0.88 |
|  |  |  | 6 |  | 199 ± 13 | 62.34 ± 0.53 |
|  | 95 | pl | 0 | 10 | — | 61.13 ± 0.72 |
|  |  |  | 6 |  | 212 ± 18 | 63.36 ± 1.23 |
|  | 100 | pl | 0 | 10 | — | 60.71 ± 1.08 |
|  |  |  | 6 |  | 210 ± 24 | 64.28 ± 2.53 |
|  | 105 | pl | 0 | 10 | — | 61.28 ± 0.44 |
|  |  |  | 6 |  | 205 ± 33 | 64.10 ± 1.27 |

TABLE 24

COMPRESSION MOLDED POLYMER BLEND.
DFDA 1137 NT 7/GERS 1085 NT/TALC (46.5/46.5/7.0)

| Formulation | ID | Stem | Time (Weeks) | N | Leak Rate (mg/yr) | Valve Delivery (mg/actuation) |
|---|---|---|---|---|---|---|
| A2 | 80 | ss | 0 | 10 | — | 57.80 ± 3.05 |
|  |  |  | 6 |  | 241 ± 26 | 61.25 ± 0.81 |
|  | 85 | ss | 0 | 10 | — | 60.00 ± 0.91 |
|  |  |  | 6 |  | 229 ± 15 | 61.72 ± 0.94 |
|  | 90 | ss | 0 | 10 | — | 60.37 ± 0.90 |
|  |  |  | 6 |  | 266 ± 34 | 62.18 ± 0.74 |
|  | 95 | ss | 0 | 10 | — | 59.91 ± 0.95 |
|  |  |  | 6 |  | 266 ± 26 | 61.84 ± 0.92 |
|  | 100 | ss | 0 | 10 | — | 59.70 ± 1.15 |
|  |  |  | 3 |  | 231 ± 30 | 61.31 ± 1.01 |
|  | 105 | ss | 0 | 10 | — | 60.59 ± 1.22 |
|  |  |  | 6 |  | 293 ± 38 | 61.76 ± 0.72 |
|  | 80 | pl | 0 | 10 | — | 58.27 ± 0.56 |
|  |  |  | 6 |  | 248 ± 24 | 57.59 ± 2.34 |
|  | 85 | pl | 0 | 10 | — | 58.17 ± 1.13 |
|  |  |  | 6 |  | 238 ± 21 | 59.03 ± 0.37 |
|  | 90 | pl | 0 | 10 | — | 57.39 ± 2.30 |
|  |  |  | 6 |  | 244 ± 19 | 57.94 ± 2.34 |
|  | 95 | pl | 0 | 10 | — | 58.69 ± 0.61 |
|  |  |  | 6 |  | 280 ± 40 | 59.20 ± 0.85 |
|  | 100 | pl | 0 | 10 | — | 58.53 ± 0.52 |
|  |  |  | 6 |  | 297 ± 30 | 59.55 ± 1.40 |
|  | 105 | pl | 0 | 10 | — | 58.88 ± 0.30 |
|  |  |  | 6 |  | 280 ± 30 | 60.89 ± 2.31 |
| B2 | 80 | ss | 0 | 10 | — | 64.01 ± 1.29 |
|  |  |  | 6 |  | 186 ± 20 | 65.56 ± 0.70 |

TABLE 24-continued

COMPRESSION MOLDED POLYMER BLEND.
DFDA 1137 NT 7/GERS 1085 NT/TALC (46.5/46.5/7.0)

| Formulation | ID | Stem | Time (Weeks) | N | Leak Rate (mg/yr) | Valve Delivery (mg/actuation) |
|---|---|---|---|---|---|---|
| | 85 | ss | 0 | 10 | — | 63.40 ± 0.71 |
| | | | 6 | | 191 ± 9 | 65.8 ± 0.92 |
| | 90 | ss | 0 | 10 | — | 63.40 ± 1.26 |
| | | | 6 | | 200 ± 16 | 65.74 ± 1.21 |
| | 95 | ss | 0 | 10 | — | 63.07 ± 0.74 |
| | | | 6 | | 197 ± 9 | 65.83 ± 0.74 |
| | 100 | ss | 0 | 10 | — | 63.02 ± 1.44 |
| | | | 6 | | 194 ± 9 | 65.51 ± 1.62 |
| | 105 | ss | 0 | 10 | — | 63.98 ± 0.64 |
| | | | 6 | | 185 ± 10 | 65.71 ± 0.98 |
| | 80 | pl | 0 | 10 | — | 61.25 ± 0.50 |
| | | | 6 | | 200 ± 19 | 62.19 ± 0.42 |
| | 85 | pl | 0 | 10 | — | 61.69 ± 0.62 |
| | | | 6 | | 197 ± 14 | 62.58 ± 1.28 |
| | 90 | pl | 0 | 10 | — | 61.43 ± 1.51 |
| | | | 6 | | 200 ± 12 | 62.77 ± 0.88 |
| | 95 | pl | 0 | 10 | — | 61.50 ± 0.57 |
| | | | 6 | | 208 ± 14 | 63.75 ± 0.91 |
| | 100 | pl | 0 | 10 | — | 62.26 ± 0.54 |
| | | | 6 | | 203 ± 10 | 64.25 ± 2.12 |
| | 105 | pl | 0 | 10 | — | 61.94 ± 0.58 |
| | | | 6 | | 188 ± 13 | 63.39 ± 0.64 |

TABLE 25

COMPRESSION MOLDED POLYMER BLEND.
DFDA 1137 NT 7/GERS 1085 NT/TALC (69.8/23.2/7.0)

| Formulation | ID | Stem | Time (Weeks) | N | Leak Rate (mg/yr) | Valve Delivery (mg/actuation) |
|---|---|---|---|---|---|---|
| A2 | 80 | ss | 0 | 10 | — | 60.31 ± 0.91 |
| | | | 6 | | 330 ± 53 | 62.18 ± 0.90 |
| | 85 | ss | 0 | 10 | — | 60.53 ± 1.09 |
| | | | 6 | | 422 ± 197 | 62.01 ± 0.70 |
| | 90 | ss | 0 | 10 | — | 59.66 ± 1.41 |
| | | | 6 | | 302 ± 59 | 62.05 ± 0.74 |
| | 95 | ss | 0 | 10 | — | 60.06 ± 1.36 |
| | | | 6 | | 333 ± 74 | 62.10 ± 0.77 |
| | 100 | ss | 0 | 10 | — | 61.05 ± 1.03 |
| | | | 6 | | 331 ± 42 | 61.70 ± 0.83 |
| | 105 | ss | 0 | 10 | — | 60.86 ± 0.93 |
| | | | 6 | | 297 ± 41 | 61.50 ± 1.01 |
| | 80 | pl | 0 | 10 | — | 58.44 ± 0.54 |
| | | | 6 | | 288 ± 41 | 58.22 ± 1.62 |
| | 85 | pl | 0 | 10 | — | 58.73 ± 0.44 |
| | | | 6 | | 303 ± 30 | 59.01 ± 0.56 |
| | 90 | pl | 0 | 10 | — | 58.79 ± 0.66 |
| | | | 6 | | 275 ± 29 | 59.52 ± 0.61 |
| | 95 | pl | 0 | 10 | — | 58.87 ± 1.21 |
| | | | 6 | | 322 ± 59 | 60.48 ± 1.39 |
| | 100 | pl | 0 | 10 | — | 59.35 ± 0.66 |
| | | | 6 | | 306 ± 33 | 61.10 ± 1.59 |
| | 105 | pl | 0 | 10 | — | 59.24 ± 0.59 |
| | | | 6 | | 302 ± 38 | 58.71 ± 3.32 |
| B2 | 80 | ss | 0 | 10 | — | 64.24 ± 0.51 |
| | | | 6 | | 230 ± 69 | 65.83 ± 0.56 |
| | 85 | ss | 0 | 10 | — | 63.78 ± 1.10 |
| | | | 6 | | 231 ± 145 | 65.94 ± 1.09 |
| | 90 | ss | 0 | 10 | — | 64.50 ± 1.30 |
| | | | 6 | | 201 ± 17 | 66.09 ± 0.66 |
| | 95 | ss | 0 | 10 | — | 62.51 ± 1.58 |
| | | | 6 | | 204 ± 19 | 66.05 ± 1.10 |
| | 100 | ss | 0 | 10 | — | 64.14 ± 0.81 |
| | | | 6 | | 202 ± 27 | 65.86 ± 0.92 |
| | 105 | ss | 0 | 10 | — | 64.41 ± 0.92 |
| | | | 6 | | 219 ± 70 | 66.38 ± 0.96 |
| | 80 | pl | 0 | 10 | — | 62.09 ± 0.49 |
| | | | 6 | | 199 ± 10 | 62.50 ± 0.59 |
| | 85 | pl | 0 | 10 | — | 61.77 ± 1.82 |

TABLE 25-continued

COMPRESSION MOLDED POLYMER BLEND.
DFDA 1137 NT 7/GERS 1085 NT/TALC (69.8/23.2/7.0)

| Formulation | ID | Stem | Time (Weeks) | N | Leak Rate (mg/yr) | Valve Delivery (mg/actuation) |
|---|---|---|---|---|---|---|
| | | | 6 | | 199 ± 16 | 64.04 ± 1.66 |
| | 90 | pl | 0 | 10 | — | 62.47 ± 0.66 |
| | | | 6 | | 202 ± 17 | 63.89 ± 1.54 |
| | 95 | pl | 0 | 10 | — | 62.50 ± 0.52 |
| | | | 6 | | 198 ± 13 | 63.87 ± 1.27 |
| | 100 | pl | 0 | 10 | — | 62.67 ± 0.64 |
| | | | 6 | | 206 ± 18 | 66.47 ± 4.74 |
| | 105 | pl | 0 | 10 | — | 62.35 ± 0.49 |
| | | | 6 | | 194 ± 12 | 63.83 ± 0.92 |

The results in TABLES 20–25 show that the indicated blends are suitable seal materials for use with metered dose inhalers containing the indicated formulations. Moreover, the data indicate that blends in all proportions would be suitable.

Diaphragms of the invention were prepared from ATTANE™ 4602 polyolefin and ATTANE™ 4701 polyolefin and tested with the formulations indicated in TABLE 26 and TABLE 27 below, respectively:

TABLE 26

COMPRESSION MOLDED ATTANE ™ 4602 POLYOLEFIN

| Formulation | ID | Stem | Time (Weeks) | N | Leak Rate (mg/yr) | Valve Delivery (mg/actuation) |
|---|---|---|---|---|---|---|
| A3 | 80 | ss | 0 | 10 | — | 62.21 ± 0.76 |
| | | | 6 | | 1442 ± 595 | 61.43 ± 1.65 |
| | 85 | ss | 0 | 10 | — | 62.37 4 1.64 |
| | | | 6 | | 1611 ± 499 | 61.31 ± 1.07 |
| | 90 | ss | 0 | 10 | — | 62.17 ± 0.65 |
| | | | 6 | | 1917 ± 1245 | 61.45 ± 1.90 |
| | 95 | ss | 0 | 10 | — | 61.71 ± 0.47 |
| | | | 6 | | 1410 ± 720 | 60.41 ± 4.32 |
| | 100 | ss | 0 | 10 | — | 61.46 ± 1.04 |
| | | | 6 | | 1177 ± 644 | 54.14 ± 16.75 |
| | 105 | ss | 0 | 10 | — | 61.78 ± 1.17 |
| | | | 6 | | 1824 ± 2007 | 61.58 ± 0.96 |
| | 80 | pl | 0 | 10 | — | 59.41 ± 0.34 |
| | | | 6 | | 285 ± 23 | 58.38 ± 0.58 |
| | 85 | pl | 0 | 10 | — | 58.74 ± 1.70 |
| | | | 6 | | 390 ± 216 | 56.81 ± 5.49 |
| | 90 | pl | 0 | 10 | — | 59.42 ± 0.62 |
| | | | 6 | | 316 ± 46 | 58.40 ± 1.08 |
| | 95 | pl | 0 | 10 | — | 59.59 ± 0.62 |
| | | | 6 | | 440 ± 430 | 56.25 ± 4.51 |
| | 100 | pl | 0 | 10 | — | 59.89 ± 0.64 |
| | | | 6 | | 328 ± 91 | 59.84 ± 1.74 |
| | 105 | pl | 0 | 10 | — | 59.38 ± 1.03 |
| | | | 6 | | 419 ± 218 | 60.04 ± 2.83 |
| B2 | 80 | ss | 0 | 10 | — | 66.53 ± 0.92 |
| | | | 6 | | 802 ± 1034 | 67.86 ± 0.81 |
| | 85 | ss | 0 | 10 | — | 66.14 ± 0.55 |
| | | | 6 | | 812 ± 425 | 66.70 ± 0.72 |
| | 90 | ss | 0 | 10 | — | 66.18 ± 1.18 |
| | | | 6 | | 812 ± 644 | 66.61 ± 0.85 |
| | 95 | ss | 0 | 10 | — | 65.97 ± 1.11 |
| | | | 6 | | 925 ± 712 | 66.76 ± 0.80 |
| | 100 | ss | 0 | 10 | — | 66.02 ± 0.98 |
| | | | 6 | | 1067 ± 1137 | 66.36 ± 1.03 |
| | 105 | ss | 0 | 10 | — | 66.29 ± 0.88 |
| | | | 6 | | 1169 ± 1462 | 66.39 ± 1.96 |
| | 80 | pl | 0 | 10 | — | 63.92 ± 0.40 |
| | | | 6 | | 163 ± 17 | 63.64 ± 0.95 |
| | 85 | pl | 0 | 10 | — | 63.72 ± 0.95 |
| | | | 6 | | 187 ± 31 | 63.93 ± 0.70 |
| | 90 | pl | 0 | 10 | — | 64.26 ± 3.81 |
| | | | 6 | | 189 ± 42 | 64.36 ± 0.82 |

TABLE 26-continued

COMPRESSION MOLDED ATTANE ™ 4602 POLYOLEFIN

| Formulation | ID | Stem | Time (Weeks) | N | Leak Rate (mg/yr) | Valve Delivery (mg/actuation) |
|---|---|---|---|---|---|---|
| | 95 | pl | 0 | 10 | — | 63.57 ± 1.13 |
| | | | 6 | | 166 ± 13 | 64.99 ± 3.07 |
| | 100 | pl | 0 | 10 | — | 63.55 ± 1.47 |
| | | | 6 | | 198 ± 38 | 65.23 ± 2.72 |
| | 105 | pl | 0 | 10 | — | 65.46 ± 2.42 |
| | | | 6 | | 2334 ± 3940 | 74.03 ± 33.09 |

TABLE 27

COMPRESSION MOLDED ATTANE ™ 4701 POLYOLEFIN

| Formulation | ID | Stem | Time (Weeks) | N | Leak Rate (mg/yr) | Valve Delivery (mg/actuation) |
|---|---|---|---|---|---|---|
| A3 | 80 | ss | 0 | 10 | — | 61.73 ± 0.81 |
| | | | 6 | | 2377 ± 394 | 60.04 ± 3.46 |
| | 85 | ss | 0 | 10 | — | 62.27 ± 0.88 |
| | | | 6 | | 2263 ± 1534 | 61.84 ± 0.71 |
| | 90 | ss | 0 | 10 | — | 62.37 ± 0.69 |
| | | | 6 | | 1817 ± 793 | 61.98 ± 0.46 |
| | 95 | ss | 0 | 10 | — | 61.81 ± 0.63 |
| | | | 6 | | 2447 ± 2861 | 61.09 ± 1.57 |
| | 100 | ss | 0 | 10 | — | 61.79 ± 0.79 |
| | | | 6 | | 2441 ± 1081 | 61.35 ± 0.94 |
| | 105 | ss | 0 | 10 | — | 61.21 ± 0.85 |
| | | | 6 | | 1480 ± 867 | 60.67 ± 0.92 |
| | 80 | pl | 0 | 10 | — | 59.51 ± 0.85 |
| | | | 6 | | 356 ± 71 | 58.45 ± 0.84 |
| | 85 | pl | 0 | 10 | — | 59.43 ± 1.31 |
| | | | 6 | | 294 ± 21 | 57.03 ± 2.39 |
| | 90 | pl | 0 | 10 | — | 59.62 ± 0.65 |
| | | | 6 | | 322 ± 59 | 58.96 ± 0.62 |
| | 95 | pl | 0 | 10 | — | 59.50 ± 0.69 |
| | | | 6 | | 297 ± 26 | 58.77 ± 1.03 |
| | 100 | pl | 0 | 10 | — | 57.92 ± 2.91 |
| | | | 6 | | 326 ± 33 | 58.49 ± 0.99 |
| | 105 | pl | 0 | 10 | — | 57.30 ± 5.32 |
| | | | 6 | | 1093 ± 1193 | 58.23 ± 0.71 |
| B2 | 80 | ss | 0 | 10 | — | 66.58 ± 1.01 |
| | | | 6 | | 617 ± 382 | 67.42 ± 1.08 |
| | 85 | ss | 0 | 10 | — | 67.25 ± 1.56 |
| | | | 6 | | 745 ± 610 | 67.40 ± 0.72 |
| | 90 | ss | 0 | 10 | — | 66.75 ± 1.01 |
| | | | 6 | | 716 ± 489 | 67.44 ± 1.01 |
| | 95 | ss | 0 | 10 | — | 66.86 ± 0.74 |
| | | | 6 | | 797 ± 602 | 67.05 ± 0.76 |
| | 100 | ss | 0 | 10 | — | 66.36 ± 0.66 |
| | | | 6 | | 1145 ± 1080 | 67.06 ± 0.41 |
| | 105 | ss | 0 | 10 | — | 66.18 ± 0.98 |
| | | | 6 | | 1020 ± 731 | 66.33 ± 0.90 |
| | 80 | pl | 0 | 10 | — | 64.11 ± 0.44 |
| | | | 6 | | 176 ± 20 | 63.87 ± 0.74 |
| | 85 | pl | 0 | 10 | — | 63.45 ± 1.06 |
| | | | 6 | | 175 ± 17 | 63.97 ± 0.79 |
| | 90 | pl | 0 | 10 | — | 64.14 ± 0.47 |
| | | | 6 | | 177 ± 16 | 63.40 ± 3.13 |
| | 95 | pl | 0 | 10 | — | 63.17 ± 2.12 |
| | | | 6 | | 200 ± 68 | 64.89 ± 1.22 |
| | 100 | pl | 0 | 10 | — | 63.96 ± 0.82 |
| | | | 6 | | 197 ± 11 | 64.09 ± 0.78 |
| | 105 | pl | 0 | 10 | — | 63.46 ± 0.58 |
| | | | 6 | | 254 ± 174 | 64.50 ± 1.25 |

The results in TABLES 26 and 27 show that diaphragms of these materials are suitable but perform notably better with the indicated albuterol sulfate and beclomethasone dipropionate formulations when used with a plastic valve stem.

For comparative purposes, diaphragms were prepared from "Buna" rubber and from butyl rubber, both materials being commonly used in commercially available metered dose inhalers. These diaphragms were tested with formulations as indicated in TABLES 28 and 29 below:

TABLE 28

BUNA RUBBER

| Formulation | ID | Stem | Time (Weeks) | N | Leak Rate (mg/yr) | Valve Delivery (mg/actuation) |
|---|---|---|---|---|---|---|
| A5 | 83 | ss | 0 | 20/12 | — | 50.56 ± 1.70 |
| | | | 4 | | 386 ± 20 | 51.11 ± 1.33 |
| | | | 12 | | 377 ± 14 | 53.82 ± 1.77 |
| | 88 | ss | 0 | 20/12 | — | 52.81 ± 1.64 |
| | | | 4 | | 347 ± 49 | 52.97 ± 1.33 |
| | | | 12 | | 392 ± 13 | 54.19 ± 2.70 |
| | 93 | ss | 0 | 20/12 | — | 53.05 ± 1.42 |
| | | | 4 | | 345 ± 12 | 51.88 ± 3.76 |
| | | | 12 | | 386 ± 13 | 54.14 ± 1.79 |
| | 98 | ss | 0 | 20/12 | — | 53.88 ± 1.80 |
| | | | 4 | | 345 ± 16 | 53.78 ± 1.02 |
| | | | 12 | | 388 ± 19 | 54.05 ± 1.14 |
| | 83 | pl | 0 | 20/12 | — | 50.62 ± 0.71 |
| | | | 4 | | 312 ± 18 | 49.00 ± 1.18 |
| | | | 12 | | 395 ± 160 | 51.02 ± 0.71 |
| | 88 | pl | 0 | 20/12 | — | 53.32 ± 1.80 |
| | | | 4 | | 335 ± 12 | 52.53 ± 2.37 |
| | | | 12 | | 380 ± 13 | 53.71 ± 0.79 |
| | 93 | pl | 0 | 20/12 | — | 51.22 ± 0.75 |
| | | | 4 | | 324 ± 19 | 49.94 ± 1.36 |
| | | | 12 | | 378 ± 22 | 51.00 ± 0.45 |
| | 98 | pl | 0 | 20/12 | — | 51.27 ± 0.60 |
| | | | 4 | | 322 ± 12 | 50.57 ± 0.62 |
| | | | 12 | | 368 ± 13 | 51.13 ± 0.63 |

TABLE 29

BUTYL RUBBER

| Formulation | ID | Stem | Time (Weeks) | N | Leak Rate (mg/yr) | Valve Delivery (mg/actuation) |
|---|---|---|---|---|---|---|
| A5 | 83 | ss | 0 | 20/12 | — | 58.56 ± 2.59 |
| | | | 4 | | 174 ± 24 | 57.98 ± 2.04 |
| | | | 12 | | 216 ± 16 | 58.13 ± 3.15 |
| | 88 | ss | 0 | 20/12 | — | 57.86 ± 2.49 |
| | | | 4 | | 152 ± 9 | 58.02 ± 1.27 |
| | | | 12 | | 197 ± 10 | 58.39 ± 3.32 |
| | 93 | ss | 0 | 20/12 | — | 59.12 ± 2.19 |
| | | | 4 | | 151 ± 8 | 58.72 ± 3.35 |
| | | | 12 | | 195 ± 9 | 58.92 ± 3.46 |
| | 98 | ss | 0 | 20/12 | — | 58.74 ± 2.54 |
| | | | 4 | | 168 ± 28 | 58.02 ± 2.14 |
| | | | 12 | | 208 ± 30 | 60.59 ± 4.11 |
| | 83 | pl | 0 | 20/12 | — | 55.92 ± 0.59 |
| | | | 4 | | 159 ± 12 | 54.45 ± 1.73 |
| | | | 12 | | 247 ± 160 | 54.62 ± 1.04 |
| | 88 | pl | 0 | 20/12 | — | 56.31 ± 0.28 |
| | | | 4 | | 169 ± 25 | 54.50 ± 3.10 |
| | | | 12 | | 218 ± 22 | 54.37 ± 2.59 |
| | 93 | pl | 0 | 20/12 | — | 56.20 ± 0.73 |
| | | | 4 | | 161 ± 14 | 54.32 ± 1.58 |
| | | | 12 | | 211 ± 15 | 55.04 ± 0.78 |
| | 98 | pl | 0 | 20/12 | — | 56.67 ± 1.11 |
| | | | 4 | | 156 ± 11 | 55.16 ± 0.43 |
| | | | 12 | | 204 ± 11 | 55.24 ± 0.78 |

The results in TABLES 28 and 29 show that, when used with the indicated formulations, "Buna" diaphragms generally exhibit leak rates higher than 300 mg/yr with generally acceptable valve delivery variability. The results also show that the butyl rubber diaphragms exhibit acceptable leak rates when used with the indicated formulations but valve delivery variability is not acceptable.

Diaphragms of the invention were prepared from the materials set forth in TABLES 30 and 31 and tested with the indicated formulations. In said TABLES, Valve "A" indicates that the valve used was a valve with a stainless steel valve stem, substantially as described herein and illustrated in the Drawing. Valve "B" indicates that the valve used was a 50 μL SPRAYMISER™ aerosol valve (Neotechnic Engineering Ltd.).

small amount of ethanol as a formulation component and the nature of the drug substance. The difference between valve A and valve B is especially clear in TABLE 31 where Valve A affords unsatisfactory valve delivery variability while valve B exhibits very low variability. Within a valve type, for example valve B, the material from which the diaphragm

TABLE 30

DIAPHRAGM PERFORMANCE WITH HFC-227 FORMULATIONS

| Formulation | Diaphragm Material | Valve | Time (Weeks) | N = 10 Leak Rate (mg/yr) ± SD | N = 5 Valve Delivery (mg/actuation) ± SD |
|---|---|---|---|---|---|
| P | GERS 1085 NT | A | 0 | — | 67.78 ± 0.51 |
| | | | 3 | 13 ± 6 | 65.22 ± 1.13 |
| | | B | 0 | — | 65.84 ± 1.14 |
| | | | 3 | 8 ± 8 | 66.08 ± 0.70 |
| | DFDA 1137 NT7/ GERS 1085 NT = 50/50 | A | 0 | — | 66.40 ± 4.30 |
| | | | 3 | 12 ± 6 | 68.34 ± 0.86 |
| | | B | 0 | — | 68.20 ± 1.02 |
| | | | 3 | 3 ± 4 | 68.68 ± 0.64 |
| | DFDA 1137 NT7/ GERS 1085 NT/ Talc = 46.5/46.5/7.0 | A | 0 | — | 69.08 ± 1.32 |
| | | | 3 | 15 ± 6 | 67.58 ± 1.70 |
| | | B | 0 | — | 69.34 ± 0.89 |
| | | | 3 | 6 ± 5 | 68.94 ± 0.36 |
| | Attane ™ 4602 | A | 0 | — | 70.72 ± 0.52 |
| | | | 3 | 11 ± 3 | 67.86 ± 1.99 |
| | | B | 0 | — | 70.70 ± 0.56 |
| | | | 3 | 32 ± 59 | 69.46 ± 3.16 |
| | Attane ™ 4701 | A | 0 | — | 70.84 ± 1.23 |
| | | | 3 | 12 ± 8 | 69.78 ± 1.57 |
| | | B | 0 | — | 70.14 ± 2.10 |
| | | | 3 | 5 ± 6 | 69.76 ± 1.42 |

TABLE 31

DIAPHRAGM PERFORMANCE WITH HFC-227 FORMULATIONS

| Formulation | Diaphragm | Valve | Time (Weeks) | N = 10 Leak Rate (mg/yr) ± SD | N = 5 Valve Delivery (mg/actuation) ± SD |
|---|---|---|---|---|---|
| A7 | GERS 1085 NT | A | 0 | — | 68.27 ± 6.23 |
| | | | * | 47 ± 9 | 40.60 ± 28.88 |
| | | B | 0 | — | 75.42 ± 1.64 |
| | | | * | 41 ± 9 | 75.60 ± 0.91 |
| | DFDA 1137 NT7/ GERS 1085 NT = 50/50 | A | 0 | — | 75.88 ± 3.74 |
| | | | * | 66 ± 56 | 21.22 ± 7.61 |
| | | B | 0 | — | 78.30 ± 1.13 |
| | | | * | 37 ± 9 | 77.92 ± 0.25 |
| | DFDA 1137 NT7/ GERS 1085 NT/ Talc = 46.5/46.5/7.0 | A | 0 | — | 74.84 ± 1.62 |
| | | | * | 50 ± 14 | 76.70 ± 2.23 |
| | | B | 0 | — | 79.70 ± 4.78 |
| | | | * | 37 ± 9 | 78.33 ± 0.71 |
| | Attane ™ 4602 | A | 0 | — | 79.10 ± 4.46 |
| | | | * | 7047 ± 4844 | 80.00 ± 1.95 |
| | | B | 0 | — | 78.60 ± 0.83 |
| | | | * | 60 ± 55 | 58.82 ± 28.9 |
| | Attane ™ 4701 | A | 0 | — | 77.44 ± 2.67 |
| | | | * | 43 ± 8 | 77.48 ± 12.02 |
| | | B | 0 | — | 76.30 ± 3.50 |
| | | | * | 30 ± 15 | 66.60 ± 13.02 |

*leak rate measured over one week during the fourth week of storage at 30° C. The valve delivery measurements, however, were made after 3 weeks of storage at 30° C.

The results in TABLES 30 and 31 indicate that these diaphragms of the invention function as seal materials for use in the dynamic pressure seal of a metered dose inhaler containing a formulation that comprises HFC-227. Furthermore, these data demonstrate the dramatic difference in valve delivery variability depending on the presence of a small amount of ethanol as a formulation component and the nature of the drug substance. The difference between valve A and valve B is especially clear in TABLE 31 where Valve A affords unsatisfactory valve delivery variability while valve B exhibits very low variability. Within a valve type, for example valve B, the material from which the diaphragm is constructed also has an important effect, which is illustrated by the results for GERS 1085 NT and the several blends on one hand, and ATTANE™ 4602 and ATTANE™ on the other hand.

The claimed invention is:

1. A device for delivering an aerosol, comprising: (i) an aerosol canister defining a formulation chamber having walls defining an aperture, and (ii) a thermoplastic elastomeric sealing member for minimizing and/or preventing escape of formulation components from said device, wherein the sealing member comprises a thermoplastic elastomer comprising a copolymer of about 80 to about 95 mole percent ethylene and a total of about 5 to about 20 mole percent of one or more comonomers selected from the group consisting of 1-butene, 1-hexene, and 1-octene and wherein said formulation chamber contains an aerosol formulation comprising 1,1,1,2-tetrafluoroethane, 1,1,1,2,3,3,3-heptafluoropropane, or a mixture thereof, in an amount effective to function as a propellant.

2. A device according to claim 1, wherein the sole comonomer is 1-butene.

3. A device according to claim 1, wherein the thermoplastic elastomer comprises a copolymer of about 80 mole percent ethylene and about 20 mole percent 1-butene.

4. A device according to claim 1, wherein the sealing member is in the form of an O-ring.

5. A device according to claim 1, wherein the sealing member is in the form of a gasket.

6. A device according to claim 1, wherein the sealing member is in the form of a tank seal.

7. A device according to claim 1, wherein said formulation is a pharmaceutical formulation comprising 1,1,1,2-tetrafluoroethane, 1,1,1,2,3,3,3-heptafluoropropane, or a mixture thereof, in an amount effective to function as an aerosol propellant, and a drug in an amount sufficient to provide a predetermined number of therapeutically effective doses for inhalation.

8. A device according to claim 7 wherein said drug is a bronchodilator or a steroid.

9. A device according to claim 7 wherein said drug is albuterol sulfate.

10. A device according to claim 7 wherein said drug is beclomethasone dipropionate.

11. A device according to claim 7 wherein said drug is pirbuterol acetate.

12. A device according to claim 7 wherein said formulation further comprises ethanol.

13. A device according to claim 1 further comprising: a tank seal having walls defining a tank seal aperture, and a metering tank of a predetermined volume and having an inlet end, an inlet aperture, and an outlet end, wherein the outlet end is in sealing engagement with the diaphragm, the valve stem passes through the inlet aperture and the tank seal aperture and is in slidable engagement with the tank seal aperture, and the tank seal is in sealing engagement with the inlet end of the metering tank, and wherein the valve stem is movable between an extended closed position, in which the inlet end of the metering tank is open and the outlet end is closed, and a compressed open position in which the inlet end of the metering tank is sealed and the outlet end is open to the ambient atmosphere.

* * * * *